(12) United States Patent
Justin et al.

(10) Patent No.: US 7,806,898 B2
(45) Date of Patent: Oct. 5, 2010

(54) MODULAR GUIDE SYSTEMS AND RELATED RASPS AND METHODS FOR RESECTING A JOINT ARTICULATION SURFACE

(75) Inventors: Daniel F. Justin, Logan, UT (US); Carlyle J. Creger, Logan, UT (US); E. Marlowe Goble, Alta, WY (US); Robert A. Hodorek, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1516 days.

(21) Appl. No.: 11/083,890

(22) Filed: Mar. 18, 2005

(65) Prior Publication Data

US 2006/0009776 A1      Jan. 12, 2006

Related U.S. Application Data

(63) Continuation-in-part of application No. 11/040,503, filed on Jan. 21, 2005, which is a continuation-in-part of application No. 10/901,941, filed on Jul. 28, 2004.

(60) Provisional application No. 60/586,706, filed on Jul. 9, 2004.

(51) Int. Cl.
*A61B 17/56* (2006.01)
(52) U.S. Cl. .......................................... 606/88; 606/85
(58) Field of Classification Search .................. 606/84, 606/85, 86 R, 87, 88, 89, 79, 82; 408/115 R; 623/20.14, 20.21
See application file for complete search history.

(56) References Cited

U.S. PATENT DOCUMENTS

| 3,748,662 A | 7/1973 | Helfet |
| 4,719,908 A * | 1/1988 | Averill et al. ................. 606/80 |
| 4,964,868 A | 10/1990 | Bloebaum |
| 5,035,699 A | 7/1991 | Coates |
| 5,037,439 A | 8/1991 | Albrektsson et al. |
| 5,100,409 A | 3/1992 | Coates et al. |

(Continued)

FOREIGN PATENT DOCUMENTS

EP      0 554 959 A1      8/1993

(Continued)

OTHER PUBLICATIONS

The extended Search Report dated Feb. 12, 2010 from related European application No. 06733764.2.

(Continued)

*Primary Examiner*—Eduardo C Robert
*Assistant Examiner*—David Comstock
(74) *Attorney, Agent, or Firm*—Baker & Daniels LLP

(57) ABSTRACT

The present invention relates to guide systems and methods for resecting at least a portion of a joint articulation surface on a bone by mounting a first cutting guide on the joint articulation surface. A first portion of the joint articulation surface is resected using the first cutting guide as a guide for resecting. A second cutting guide is then mounted on the joint articulation surface following which the first cutting guide is removed. A second portion of the joint articulation surface is then resected using the second cutting guide template as a guide for resecting, at least a section of the second portion of the joint articulation surface having been previously covered by the first guide template.

28 Claims, 20 Drawing Sheets

U.S. PATENT DOCUMENTS

| | | | |
|---|---|---|---|
| 5,176,684 | A | 1/1993 | Ferrante et al. |
| 5,312,408 | A | 5/1994 | Brown |
| 5,334,205 | A | 8/1994 | Chain |
| 5,344,423 | A | 9/1994 | Dietz et al. |
| 5,346,496 | A | 9/1994 | Pennig |
| 5,364,402 | A * | 11/1994 | Mumme et al. ............... 606/88 |
| D357,315 | S | 4/1995 | Dietz |
| 5,413,606 | A | 5/1995 | Fisk et al. |
| 5,417,695 | A | 5/1995 | Axelson, Jr. |
| 5,474,559 | A | 12/1995 | Bertin et al. |
| 5,484,446 | A | 1/1996 | Burke et al. |
| 5,486,180 | A | 1/1996 | Dietz et al. |
| 5,578,039 | A * | 11/1996 | Vendrely et al. ............. 606/88 |
| D376,202 | S | 12/1996 | Burke et al. |
| 5,609,642 | A | 3/1997 | Johnson et al. |
| 5,634,927 | A | 6/1997 | Houston et al. |
| 5,642,550 | A * | 7/1997 | Maruyama et al. ........... 15/102 |
| 5,653,714 | A | 8/1997 | Dietz et al. |
| 5,709,689 | A | 1/1998 | Ferrante et al. |
| 5,735,856 | A * | 4/1998 | McCue et al. ................. 606/87 |
| 5,743,915 | A | 4/1998 | Bertin et al. |
| 5,755,803 | A | 5/1998 | Haines et al. |
| 5,769,855 | A | 6/1998 | Bertin et al. |
| 5,860,981 | A | 1/1999 | Bertin et al. |
| 5,871,539 | A | 2/1999 | Pappas |
| 5,885,035 | A | 3/1999 | Hoffschneider |
| 5,908,424 | A | 6/1999 | Bertin et al. |
| 6,063,091 | A | 5/2000 | Lombardo et al. |
| 6,132,468 | A | 10/2000 | Mansmann |
| 6,159,216 | A | 12/2000 | Burkinshaw et al. |
| 6,355,045 | B1 | 3/2002 | Gundlapalli et al. |
| 6,436,101 | B1 | 8/2002 | Hamada |
| 6,478,799 | B1 * | 11/2002 | Williamson ................... 606/90 |
| 6,482,209 | B1 | 11/2002 | Engh et al. |
| 6,554,838 | B2 | 4/2003 | McGovern et al. |
| 6,620,168 | B1 | 9/2003 | Lombardo et al. |
| 6,712,824 | B2 | 3/2004 | Millard et al. |
| 6,969,393 | B2 | 11/2005 | Pinczewski et al. |
| 2002/0019637 | A1 | 2/2002 | Frey et al. |
| 2002/0198528 | A1 | 12/2002 | Engh et al. |
| 2003/0028196 | A1 | 2/2003 | Bonutti |
| 2003/0130665 | A1 | 7/2003 | Pinczewski et al. |
| 2005/0143831 | A1 | 6/2005 | Justin et al. |
| 2005/0192588 | A1 | 9/2005 | Garcia |
| 2006/0009854 | A1 | 1/2006 | Justin |
| 2006/0167460 | A1 | 7/2006 | Pinczewski et al. |
| 2006/0200161 | A1 | 9/2006 | Plaskos et al. |
| 2006/0276796 | A1 | 12/2006 | Creger |
| 2006/0293682 | A1 | 12/2006 | Justin |
| 2007/0288029 | A1 | 12/2007 | Justin |

FOREIGN PATENT DOCUMENTS

| | | |
|---|---|---|
| EP | 0600806 A1 | 6/1994 |
| EP | 0681817 A1 | 11/1995 |
| EP | 0 502 737 B1 | 9/2002 |
| EP | 1550419 A2 | 7/2005 |
| FR | 2445136 A1 | 7/1980 |
| FR | 2521421 A1 | 8/1983 |
| FR | 2682589 | 4/1993 |
| FR | 2833479 A1 | 6/2003 |
| WO | WO 91/06260 | 5/1991 |
| WO | WO91/06260 A1 | 5/1991 |
| WO | WO 98/04202 | 2/1998 |
| WO | WO 2004/002332 A1 | 1/2004 |
| WO | WO2004/058108 A1 | 7/2004 |
| WO | WO 2005/069809 A3 | 8/2005 |

OTHER PUBLICATIONS

The Office Action mailed Jan. 12, 2009 in related British application No. GB0710667.7.

The Response filed May 12, 2009 to the Office Action mailed Jan. 12, 2009 in related British application No. GB0710667.7.

The International Preliminary Report on Patentability mailed Aug. 2, 2007 in related International application No. PCT/US2006/000875.

The International Preliminary Report on Patentability mailed Jan. 21, 2005 in related International application No. PCT/US2006/001026.

* cited by examiner

MODULAR GUIDE SYSTEMS AND RELATED RASPS AND METHODS FOR RESECTING A JOINT ARTICULATION SURFACE

CROSS-REFERENCE TO RELATED APPLICATIONS

This application is a continuation-in-part of U.S. patent application Ser. No. 11/040,503, filed Jan. 21, 2005, which is a continuation-in-part of U.S. patent application Ser. No. 10/901,941, filed Jul. 28, 2004, which claims priority to U.S. Provisional Application Ser. No. 60/586,706, filed Jul. 9, 2004, which applications are incorporated herein by specific reference.

BACKGROUND OF THE INVENTION

1. The Field of the Invention

The present invention relates to guide systems and related rasps and methods for resecting at least a portion of a joint articulation surface on a bone and mounting an implant thereat.

2. The Relevant Technology

The human body has a variety of movable orthopedic joints such as the knee joint, hip joint, shoulder joint, and the like. These joints are formed by the intersection of two bones. The intersecting end of each bone has a smooth articular surface that is comprised of articular cartilage. As a result of injury, wear, arthritis, disease or other causes, it is occasionally necessary to replace all or part of an orthopedic joint with an artificial implant. This procedure is referred to as a joint replacement or arthroplasty. For example, a total knee arthroplasty comprises cutting off or resecting the articular surfaces at both the distal end of the femur and the proximal end of the tibia. Complementary artificial implants are then mounted on the distal end of the femur and the proximal end of the tibia. Where only a portion of a joint is damaged, a partial joint arthroplasty can be performed. In this procedure, one or more artificial implants replace only a portion of a joint.

Although joint replacement is now a common procedure that has met with popular success, conventional implants and related mounting techniques have significant shortcomings. One significant drawback of many joint replacements is the extended and painful patient recovery. For example, a traditional knee replacement requires an open procedure wherein a relatively large incision is made which severs a portion of the muscle bounding the femur. The large incision is made so as to fully expose the respective ends of the femur and tibia.

This exposure is necessary when using conventional techniques to resect the femur and tibia and to mount the implants. For example, resecting the femur and tibia is typically accomplished by a reciprocating saw which requires substantially full exposure of the respective ends of the femur and tibia. Furthermore, some conventional tibial implants are screwed directly into the resected end face of the tibia. Mounting such screws again requires substantially full exposure of the resected end face. In yet other embodiments, the implants are formed with posts projecting therefrom. The posts are received within sockets formed on the resected end face of the tibia and femur. Forming of the sockets and inserting the posts into the sockets requires substantially full exposure of the resected end face of the tibia and femur.

Substantially the same procedures are often used when resurfacing only a portion of a joint articulation surface. That is, the joint is exposed and a reciprocating saw is used to resect half or a portion of the articular cartilage. The implant is then mounted by using screws or posts. Thus, even in procedures where only a portion of the joint articulation surface is being resurfaced, conventional procedures make an invasive retraction of the soft tissue and remove a large portion of the bone.

In general, the more invasive the surgery, the more painful, difficult, and time consuming the patient recovery. Furthermore, extensive resection of bone not only increases bone trauma but can also make subsequent replacement operations more difficult.

Accordingly, what is needed are systems and methods for preparing a joint articulation surface to receive an implant which are easy to use while minimizing the impact on soft tissue and the amount of bone resection. What is also needed are implants which can be used with such systems that can be mounted with minimum trauma.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to guide systems and related rasps for use in resecting an articulation surface of an orthopedic joint so that an implant can be mounted on the resected surface. As used in the specification and appended claims, the term "articulation surface" is broadly intended to include all surfaces of natural articular cartilage forming a portion of an orthopedic joint and all articulation wear surfaces of a bone forming a portion of orthopedic joint which as a result of wear, trauma, disease or other causes have all or a portion of the natural articular cartridge removed.

In the below illustrated embodiment of the present invention, guide systems and related rasps are shown which are specifically designed for mounting a trochlear groove implant at the distal end of a femur. It is appreciated, however, that the illustrated embodiments are simply examples of the present invention and that the same technology can also be used for resecting a portion of the articulation surface on a variety of other joint surfaces to receive a variety of other different types of implants. By way of example and not by limitation, the present invention can be used for resurfacing an articulation surface of a knee joint, ankle joint, hip joint, shoulder joint, elbow joint, wrist joint, interfrangial joint, or other joints. As such, the guide systems and rasps of the present invention can be used for preparing the articulation surface at the proximal or distal end of the femur, tibia, humors, radius, and ulna and on other articulation surfaces of the scapula, pelvis, bones within the foot and hand, and other bone articulation surfaces.

Figure 1:
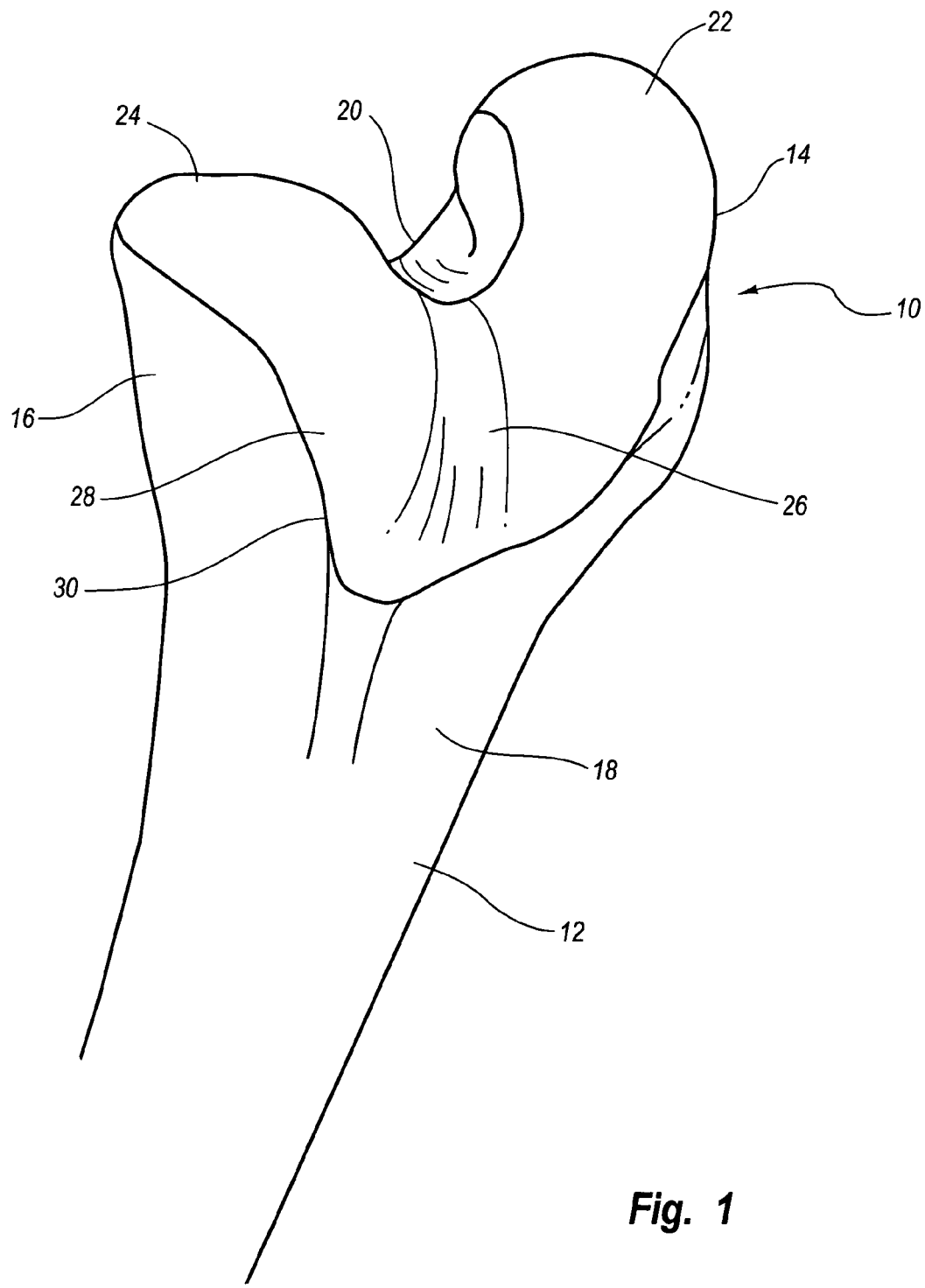
FIG. 1 is a perspective view of the distal end of a femur having a trochlear groove.

Depicted in FIG. 1 is a distal end 10 of a femur 12. Distal end 10 has a medial side 14 and a lateral side 16 that each extend between an anterior side 18 and a posterior side 20. Distal end 10 of femur 12 terminates at a lateral condyle 24 and a medial condyle 22 with a trochlear groove 26 disposed therebetween. Articular cartridge 28 defines an articulation surface for distal end 10 of femur 12. Articular cartridge 28 terminates at a margin 30.

Trochlear groove 26 is a channel that guides the movement of the patella as the knee flexes. On occasion, due to arthritis, disease, trauma, or the like, it is necessary to replace a portion of the femur forming the trochlear groove. In the depicted embodiment of the present invention, the illustrated guide systems and related rasps are designed to form a recessed pocket on femur 12 at the location of trochlear groove 26 so that an implant can be mounted within the recessed pocket.

Figure 2:
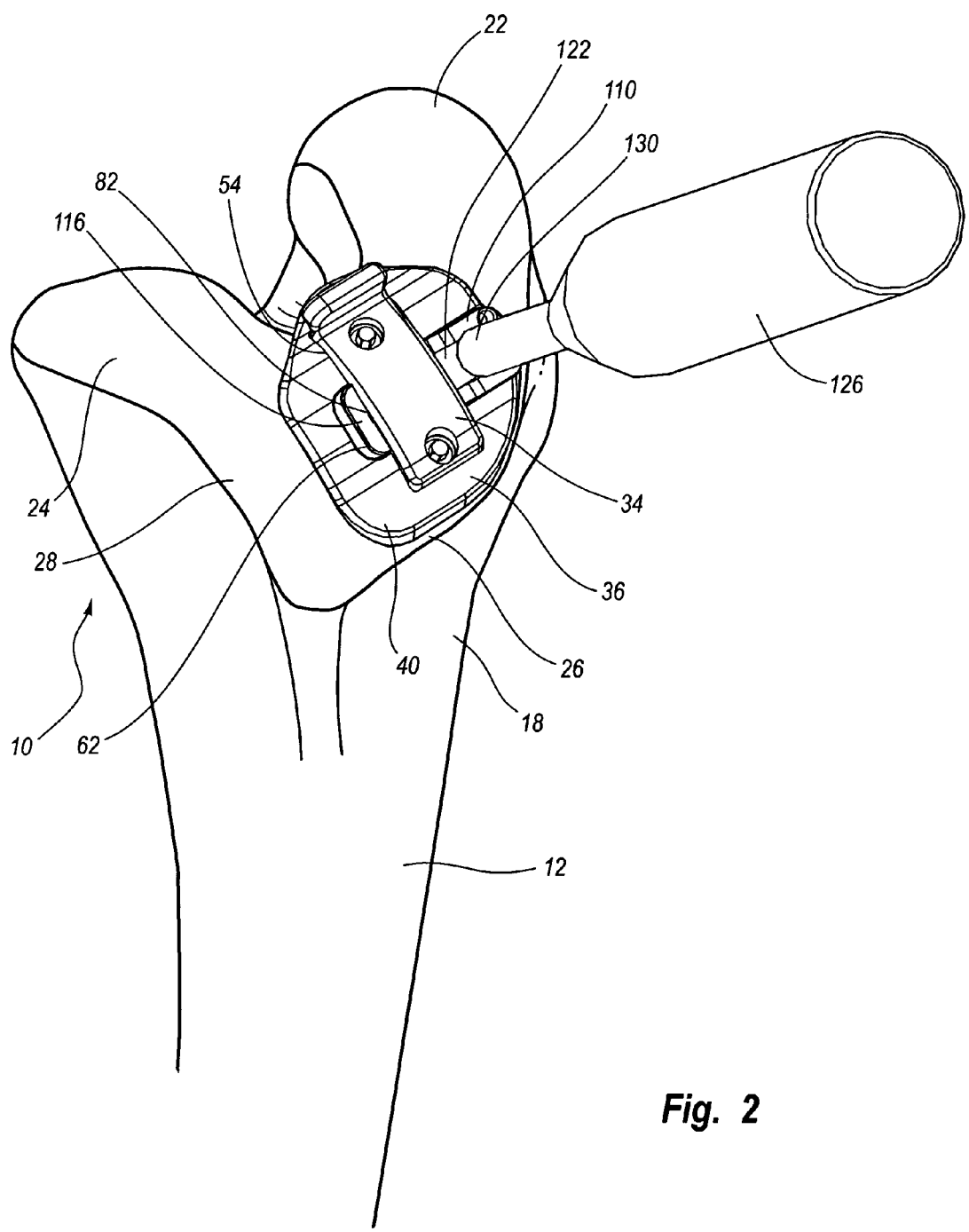
FIG. 2 is a perspective view of the femur shown in FIG. 1 having an assembly including a mounting template, a first cutting guide, and a locking brace positioned thereon.
Figure 3:
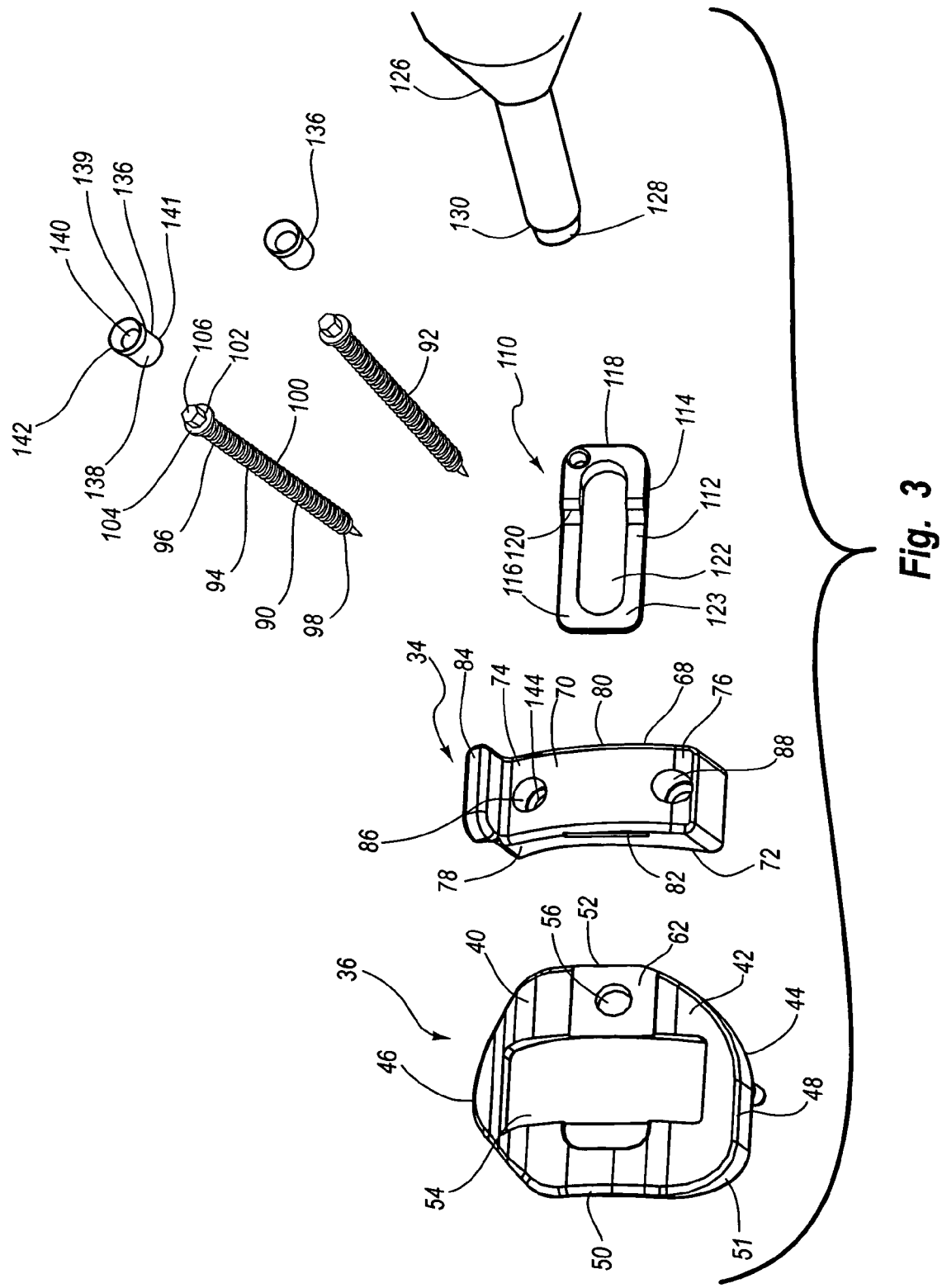
FIG. 3 is an exploded top perspective view of the assembly shown in FIG. 2.
Figure 4:
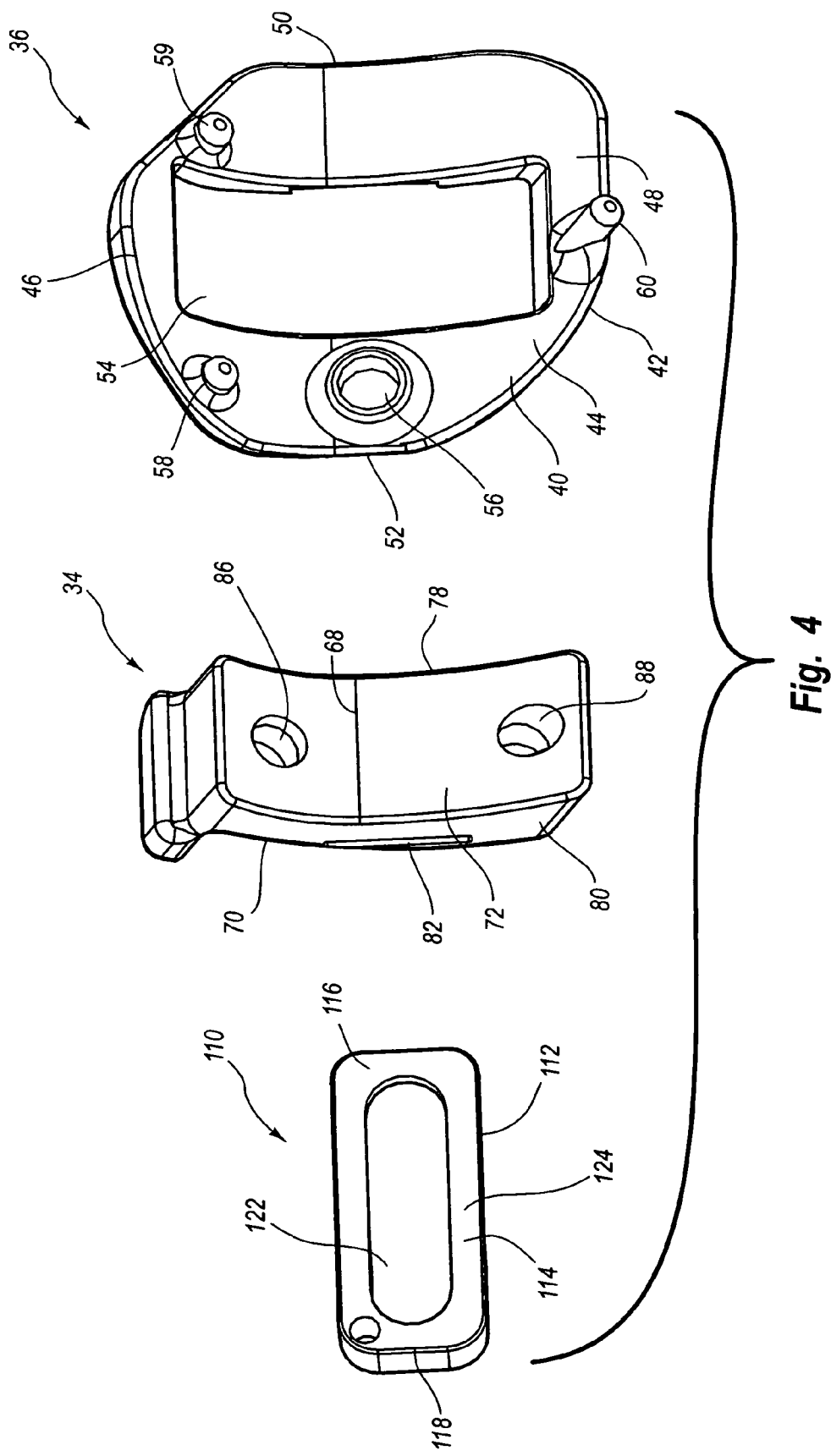
FIG. 4 is a bottom perspective view of a portion of the assembly shown in FIG. 3.

Depicted in FIG. 2, a first cutting guide 34 is shown mounted on femur 12 over trochlear groove 26. First cutting guide 34 is positioned using a mounting template 36 and a locking brace 110. As depicted in FIGS. 3 and 4, mounting template 36 comprises a base 40 having a top surface 42 and an opposing bottom surface 44. Base 40 has a first end 46 and an opposing second end 48 that each extend between opposing sides 50 and 52.

In one embodiment, base 40 comprises a plate having a substantially continuous arch extending from first end 46 to opposing second end 48. That is, bottom surface 44 has a substantially constant concave curvature while the top surface 42 has a substantially constant convex curvature. This configuration helps to minimize the size of mounting template 36 to facilitate greatest ease of insertion during use. In alternative embodiments, however, one or both of top surface 42 and bottom surface 44 can be flat or have any other desired configuration.

In the embodiment depicted, base 40 has a perimeter edge 51 that is sized and shaped comparable to the final implant. This enables the user to visually ensure that the selected position for first cutting guide 34 using mounting template 36 will eventually result in the implant replacing all of the desired area of femur 12. In the depicted embodiment, perimeter edge 51 has an asymmetric, generally circular configuration with a few spaced linear sections. In alternative embodiments, however, it is appreciated that base 40 can be any desired configuration such as circular, square, rectangular, polygonal, or any other desired shape.

Extending through base 40 between top surface 42 and bottom surface 44 is an elongated opening 54. In the embodiment depicted opening 54 has a substantially rectangular configuration and is oriented so as to extend between first end 46 and opposing second end 48. As will be discussed below in greater detail, opening 54 is size to receive first cutting guide 34. A recessed track 62 is formed on top surface 42 and transversely extends between sides 50 and 52 across opening 54. A coupling hole 56 is formed on track 62 and extends between surfaces 42 and 44 adjacent to opening 54.

Projecting from bottom surface 44 of base 40 are three support legs 58, 59, and 60. Support legs 58 and 59 are shown disposed towards first end 46 while support leg 60 is disposed toward second end 48. In alternative embodiments, it is appreciated that support legs 58-60 can be placed at a variety of different orientations. Support legs 58-60 are configured so that support base 40 can be placed in a stable orientation spaced above femur 12. Specifically, the area surrounding trochlear groove 26 has an irregular configuration due to the irregular configuration of medial condyle 22, lateral condyle 24, and trochlear groove 26. In contrast to trying to configure base 40 to precisely fit on trochlear groove 26, the use of three support legs 58-60 provides a stable platform that can be easily designed to support mounting template 36 in a stable fashion on a plurality of different sized and shaped femurs.

As depicted in FIG. 2, base 40 is supported on femur 12 as a result of support leg 58 resting against medial condyle 22, support leg 59 resting against lateral condyle 24, and support leg 60 resting against the articulation surface 28 within trochlear groove 26. In one alternative embodiment base 40 can be sized so that support leg 60 rests against anterior surface 18 outside of articulation surface 28.

In other embodiments, support legs 58-60 can be positioned at different locations on base 40 and can have a variety of different sizes and shapes. Furthermore, fewer or more support legs can be used. For example, mounting template 36 can be designed with two support legs so that the two support legs and a portion of base 40 rest directly against femur 12. In yet other embodiments, four or more support legs can be formed projecting from body 40.

As also depicted in FIGS. 3 and 4, first cutting guide 34 comprises a body 68 having a top surface 70 and a bottom surface 72 each extending between a first end 74 and an opposing second end 76. Also extending between opposing ends 74 and 76 is a first side wall 78 and a second side wall 80. Side walls 78 and 80 are substantially linear and are disposed in parallel alignment. Body 68 generally has a substantially rectangular, parallelepiped configuration except that top surface 70 and bottom surface 72 have a generally constant curvature extending between opposing ends 74 and 76. In alternative embodiments surfaces 70 and 72 need not be curved but can be flat or other desired configurations. However, curvature of surface 70 and 72 helps to minimize size. An engagement slot 82 transversely extends through body 68 between opposing side walls 78 and 80. Upwardly projecting from first end 74 of body 68 is a stop 84.

In one embodiment of the present invention, means are provided for securing first cutting guide 34 to femur 12 independent of mounting template 36. By way of example and not by limitation, extending through first cutting guide 34 from top surface 70 to bottom surface 72 are spaced apart mounting holes 86 and 88. Fasteners are designed to pass through mounting holes 86 and 88 and engage femur 12 so as to secure first cutting guide 34 to femur 12.

In the depicted embodiment, the fasteners comprise threaded screws 90 and 92. Each screw 90 and 92 comprises an elongated shaft 94 having a first end 96 and an opposing second end 98. Threads 100 are formed along shaft 94 while an enlarged head 102 is formed at first end 96. In the embodiment depicted, enlarged head 102 comprises a flange 104 that encircles and radially outwardly projects from first end 96. An engagement head 106 extends above flange 104 and has a polygonal or non-circular cross section so that a driver can be connected to engagement head 106 for selective rotation of screws 90 and 92.

It is appreciated that enlarged head 102 can be formed with a socket, slot(s), or other engaging surfaces to engage with other types of drivers. Each screw 90, 92 is configured so that second end 98 can be received within and slid through a corresponding mounting hole 86, 88 of first cutting guide 34. Enlarged head 102 is larger than mounting holes 86 and 88 and thus function as a stop. In alternative embodiments, screws 90 and 92 can be replaced with other conventional forms of fasteners such as bone anchors, expansion bolts, barbed shafts, and the like.

As depicted in FIG. 2, locking brace 110 is used to selectively secure first cutting guide 34 to mounting plate 36. As depicted in FIGS. 3 and 4, locking brace 110 has a top surface 112 and an opposing bottom surface 114 that each extend between a first end 116 and opposing second end 118. Bottom surface 114 is substantially flat while top surface 112 has a centrally formed shoulder 120. As a result of shoulder 120, second end 118 of locking brace 110 is thicker than first end 116. An elongated slot 122 extends between top surface 123 and bottom surface 124 along the length of locking brace 110.

Returning to FIG. 2, during use first end 116 of locking brace 110 is advanced through engagement slot 82 of first cutting guide 34. First cutting guide 34 is then positioned within opening 54 on mounting template 36 such that locking brace 110 is received within recessed track 62 on mounting template 36. It is noted that locking brace 110 passes through first cutting guide 34 so that locking brace 100 rests against mounting template 36 on each side of opening 54. In this position, slot 122 is aligned with coupling hole 56 on mounting template 36. An elongated handle 126 has a tip 128 and an enlarged shoulder 130 outwardly projecting proximal of tip 128 (FIG. 3). In one embodiment, tip 128 and coupling hole 56 are threaded so that tip 128 can be threaded into coupling hole 56. Enlarged shoulder 130 is larger than the diameter of slot 122 in locking brace 110. As such, as tip 128 is threaded into coupling hole 56, shoulder 130 biases against top surface 112 of locking brace 110, thereby releasably securing first cutting guide 34 to mounting plate 36.

It is appreciated that there are a variety of alternative structural configurations that can be used to releasably secure first cutting guide 34 to mounting template 36. By way of example and not by limitation, it is appreciated that locking brace 110 can connect to each of first cutting guide 34 and mounting template 36 using the same or different coupling techniques such as frictional engagement, interlocking structures, threaded fastener, expansion bolt, or other types of fasteners.

Once cutting guide 34 is removable secured to mounting template 36, mounting template 36 is then used to properly align first cutting guide 34 on articulation surface 28. Specifically, as previously discussed, mounting template 36 is generally aligned by sight by placing support leg 58 on medial condyle 22, support leg 59 on lateral condyle 24, and aligning support leg 60 with trochlear groove 26. In this position, first cutting guide 34 is also generally aligned within the trochlear groove 26. Furthermore, where mounting template 36 is configured so as to have the same configuration as the final implant, mounting template 36 is also oriented so as to cover all of the area that is desired to be resurfaced. Once mounting template 36 is appropriately positioned, screws 90 and 92 are passed through correspondence holes 86 and 88 on first cutting guide 34 so as to rigidly fix first cutting guide 34 in the desired orientation.

In one embodiment, screws 90 and 92 can be used in association with guide sleeves. By way of example, a pair of guide sleeves 136 is depicted in FIG. 3. Each guide sleeve 136 comprises a tubular stem 138 having a first end 139 and an opposing second end 141. A passageway 140 centrally extends through stem 138 between opposing ends 139 and 141. A flange 142 encircles and radially outwardly projects from first end 139 of stem 138. Each guide sleeve 136 is configured so that second end 141 can be received within and slide through a corresponding mounting hole 86 and 88. In the depicted embodiment, each mounting hole 86 and 88 is counter bored so as to form an internal constricting shoulder 144. Flange 142 is sized to rest on shoulder 144 so as to prevent guide sleeve 136 from passing completely through mounting holes 86 and 88.

In part, guide sleeves 136 function as guides for screws 90, 92. That is, as a result of support legs 58-60, bottom surface 72 of first cutting guide 34, and thus the bottom of mounting holes 86 and 88, are spaced above femur 12. As previously discussed, this configuration helps ensure a proper and stable placement of first cutting guide 34. However, as a result of this gap or space between the bottom of mounting holes 86, 88 and femur 12, there is a potential for screws 90, 92 to become misaligned from the central longitudinal axis of each corresponding mounting hole 86, 88 as the screws 90, 92 are passed from the mounting hole 86, 88 to femur 12. This misalignment can cause binding of screws 90, 92 against first cutting guide 34 which in turn can cause unwanted displacement or improper securing of first cutting guide 34. By using guide sleeves 136 which extend from mounting holes 86, 88 to or adjacent to femur 12, guide sleeves 136 help maintain proper orientation and alignment of each screw 90, 92.

Figure 5:
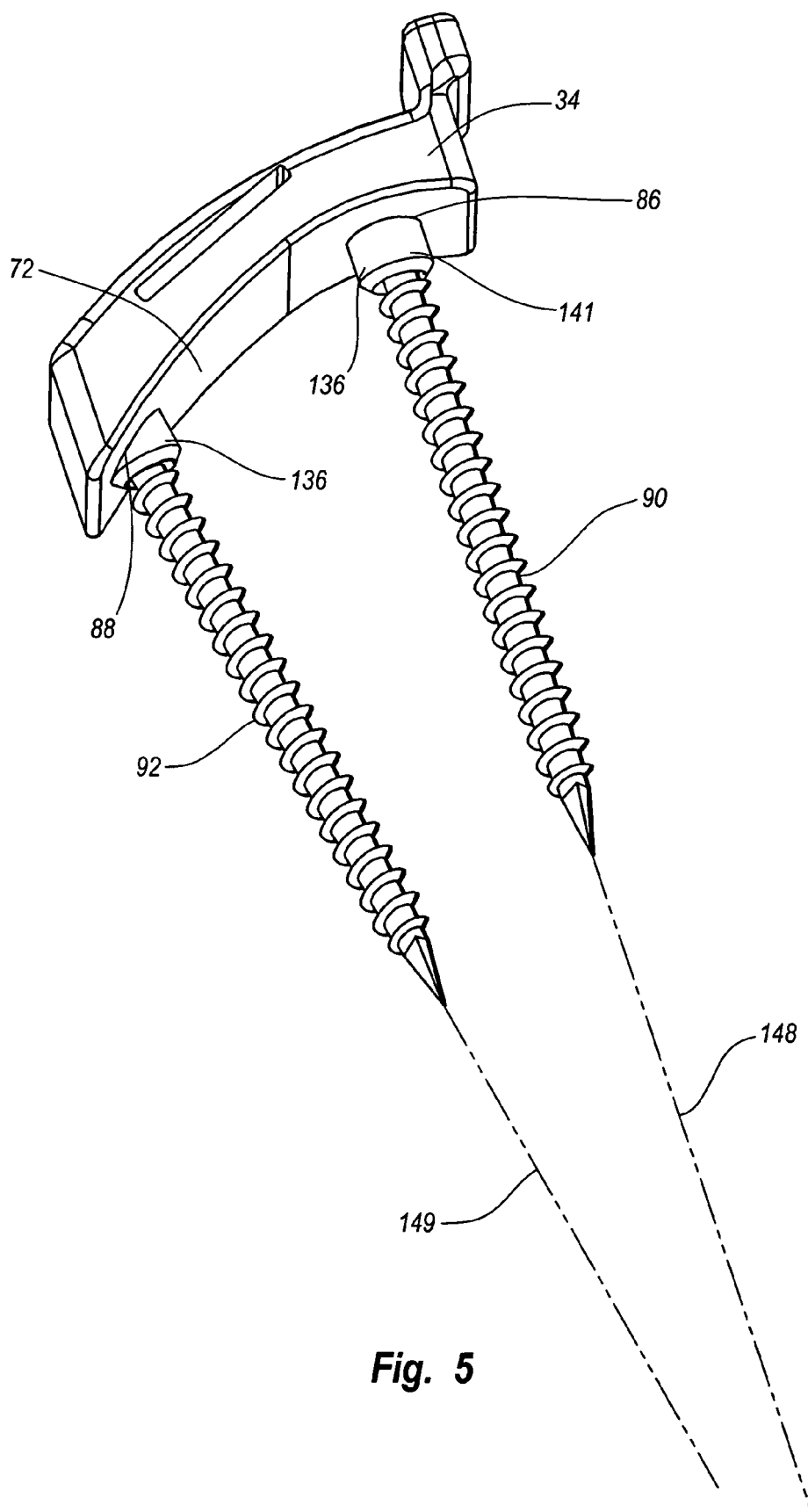
FIG. 5 is a side perspective view of the first cutting guide shown in FIG. 2.

Specifically, once mounting template 36 and first cutting guide 34 are appropriately positioned, each guide sleeve 136 is advanced through a corresponding mounting hole 86 and 88 so that second end 141 of each guide sleeve 136 is disposed adjacent to or butts against articulation surface 28. FIG. 5 shows guide sleeves 136 projecting below bottom surface 72 of first cutting guide 34. Screws 90, 92 are then passed through guide sleeves 136 and screwed into femur 12. Screws 90, 92 are advanced until flange 102 biases against the first end of each guide sleeve 136, thereby securely fixing each guide sleeve 136 to femur 12. It is noted that flange 142 of guide sleeves 136 need not bias directly against first cutting guide 34. Flange 142 primarily functions to prevent guide sleeves 136 from falling through mounting holes 86, 88 during placement of first cutting guide 34. In alternative embodiments, flange 142 can be eliminated.

Here it is noted that each mounting hole 86 and 88 has a central longitudinal axis 148 and 149 (FIG. 5), respectively, along which each screw 90, 92 is intended to extend. Mounting holes 86 and 88 are oriented at different angles relative to each other so that merely screwing screws 90 and 92 into femur 12 through guide sleeves 136 positioned within mounting holes 86, 88 cause first cutting template 34 to be locked in place. That is, it is not necessary for screws 90 and 92 to downwardly bias directly against first cutting guide 34 to secure first cutting 34 relative to femur 12. Due to the offset angles of screws 90, 92 and thus the offset angles of the guide sleeves 136, it is sufficient if the screws 90, 92 merely secure guide sleeves 136 in place to lock first cutting guide 34 in place.

Figure 6:
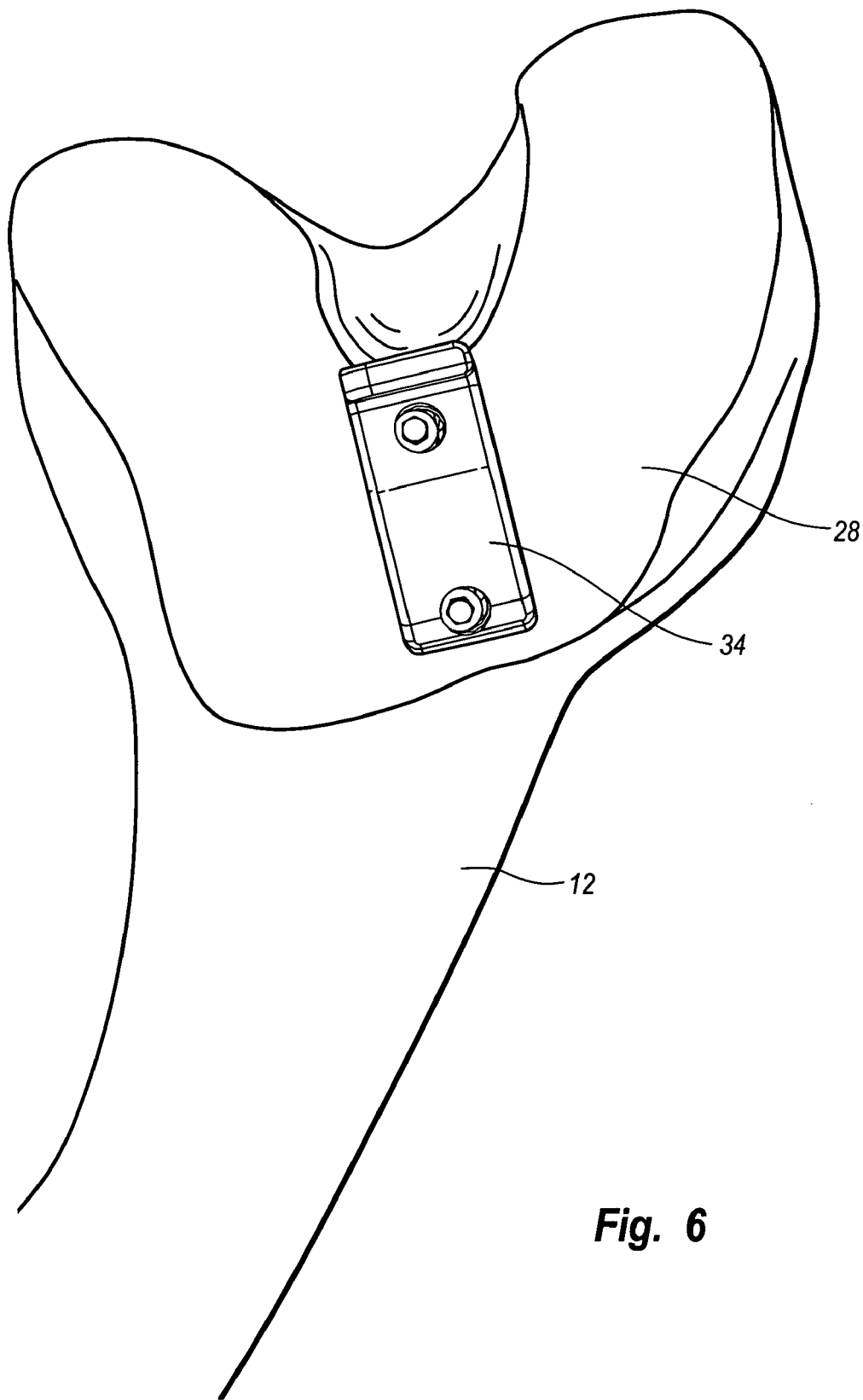
FIG. 6 is a perspective view of the first cutting guide shown in FIG. 1 mounted on the femur with the mounting template removed.

Once each screw 90, 92 is secured in place so that first cutting guide 34 is secured in pace, locking brace 110 and mounting template 136 are removed from first cutting guide 34. This is accomplished by simply unscrewing handle 126, sliding locking brace 110 out of slot 82, and then lifting off mounting template 36. As depicted in FIG. 6, first cutting guide 34 is then securely fixed to femur 12 at the appropriate location.

Figure 7:
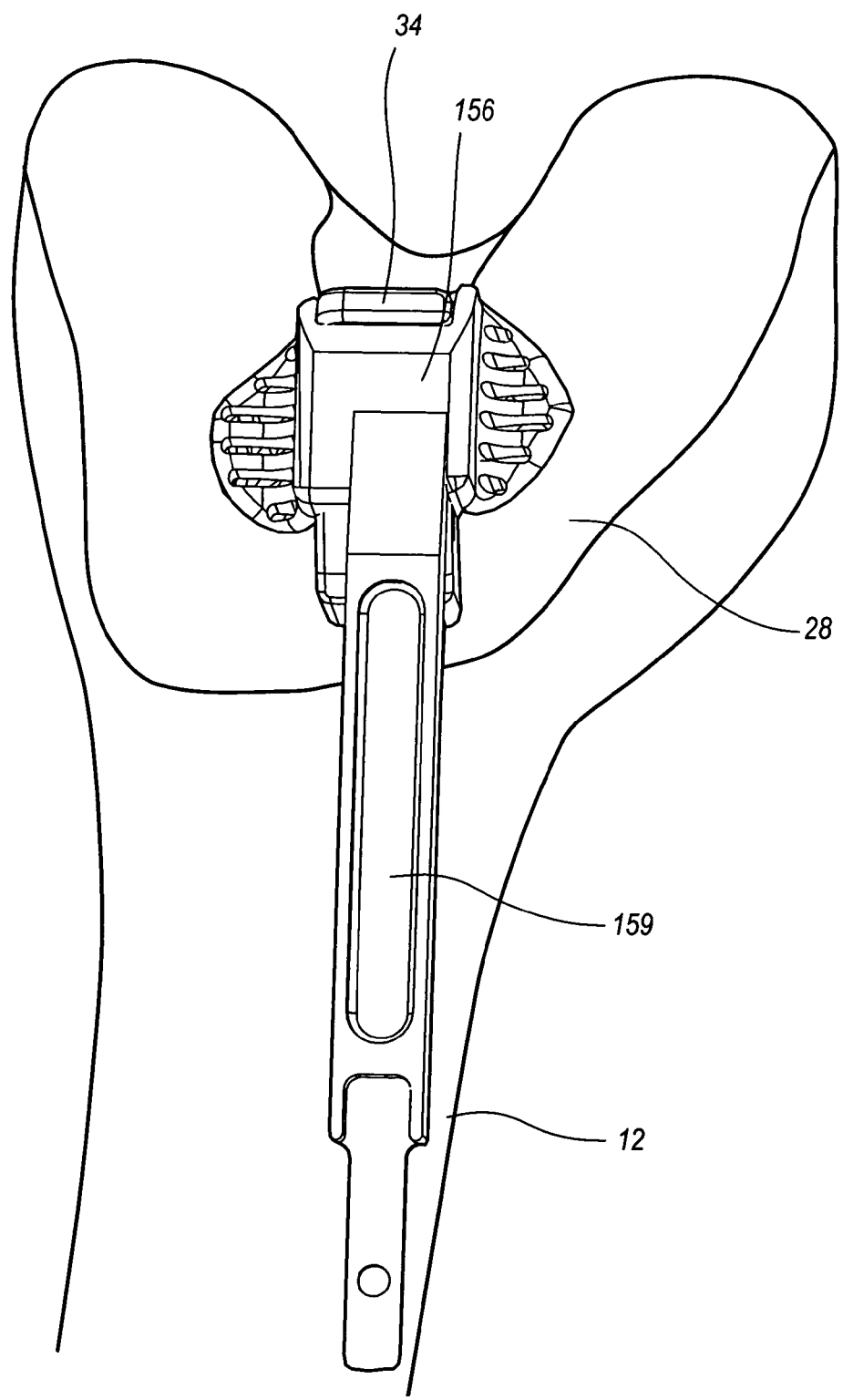
FIG. 7 is a perspective view of the femur shown in FIG. 6 having a first rasp mounted on the first cutting guide.
Figure 8:
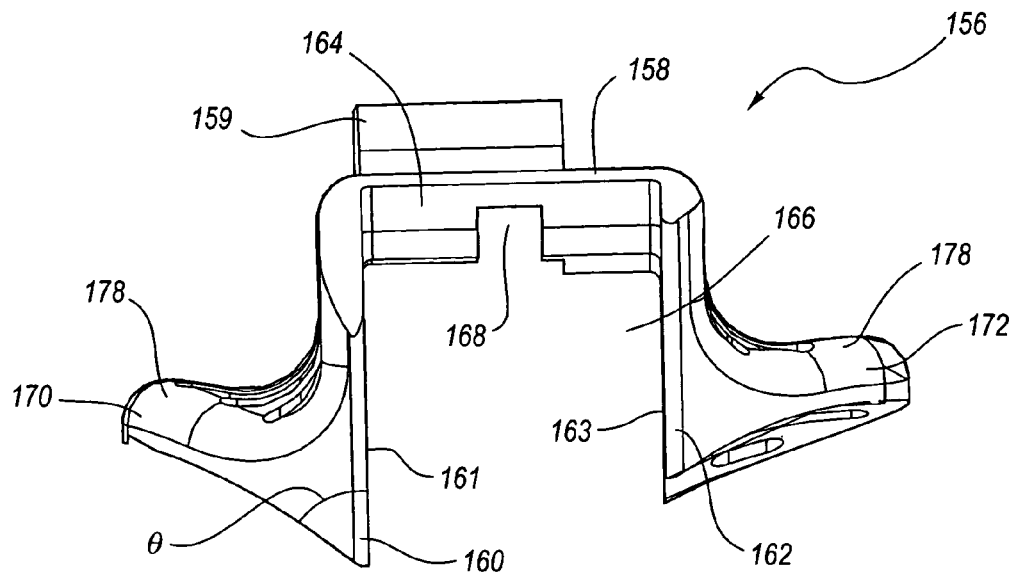
FIG. 8 is an elevated front view of the rasp shown in FIG. 7.
Figure 9:
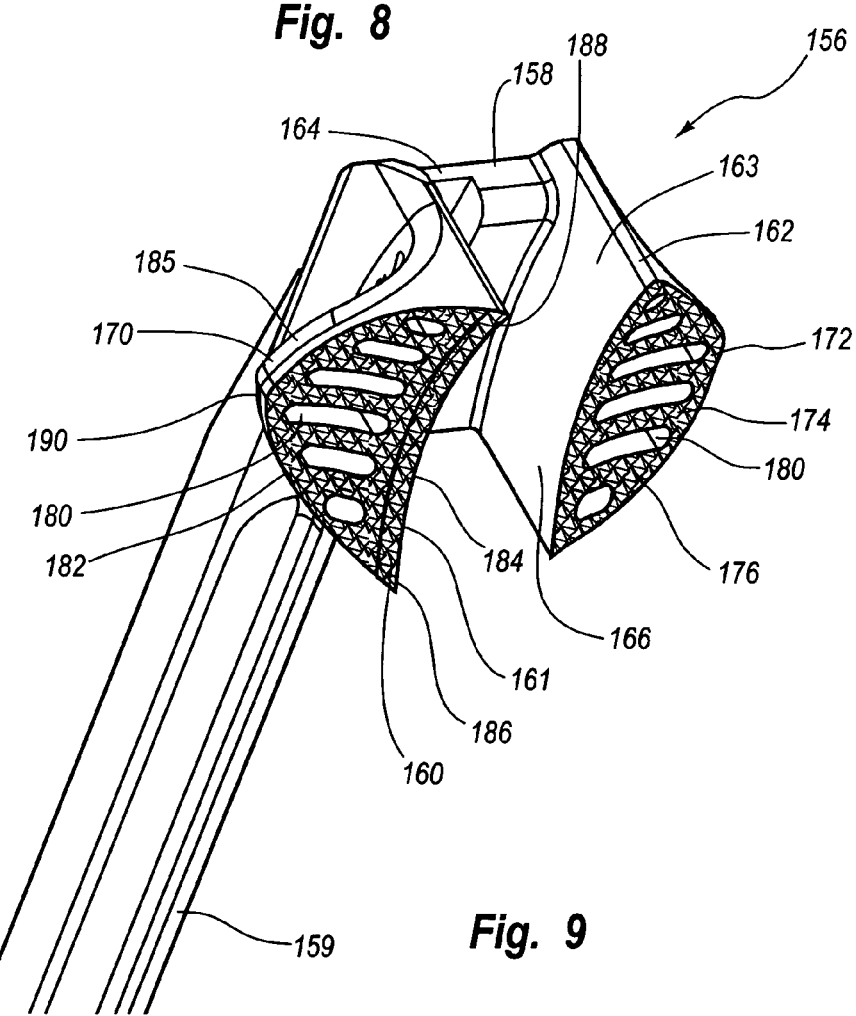
FIG. 9 is a bottom perspective view of the rasp shown in FIG. 7.

Turning to FIG. 7, a rasp 156 is now used in conjunction with first cutting guide 34 to remove a first portion of articulation surface 28 that is adjacent to first cutting guide 34. As depicted in FIGS. 8 and 9, rasp 156 comprises a body 158 having an elongated handle 159 projecting therefrom. Body 158 comprises a pair of opposing side walls 160 and 162 with a top wall 164 extending therebetween. Each of side walls 160 and 162 has an interior surface 161 and 163, respectively. Each of interior surfaces 161 and 163 are substantially planer and are disposed in substantially parallel alignment. Interior surfaces 161 and 163 bound a channel 166 that longitudinally extends through body 158. Channel 166 is configured to receive first cutting guide 34 in relatively close tolerance such that rasp 156 can be reciprocally moved along first cutting guide 34 while first cutting guide 34 functions as a guide for rasp 156. Stop 84 on first cutting guide 34 prevents rasp 156 from extending too far along first cutting guide 34.

In one embodiment, a notch 168 is formed on top wall 164 so that enlarged head 102 of screws 90, 92 can slide within notch 168. In alternative embodiments, enlarged heads 102 can be counter-sunk so as not to project above first cutting guide 34. Outwardly projecting from each of side walls 160 and 162 is a cutting head 170 and 172, respectively. Each cutting head 170 and 172 has a cutting surface 174 which is comprised of a plurality of cutting teeth 176. Each cutting head 170 and 172 also has a top surface 178 with a plurality of apertures 180 extending between cutting surface 174 and top surface 178. Apertures 180 enable the removal of the bone particles that are shaved off by cutting teeth 176.

Each cutting surface 174 has a perimeter edge 182 having a generally semicircular configuration. Perimeter edge 182 includes a linear inside edge 184 and a curved outside edge 185. Inside edge 184 extends along interior surface 161 between a first end 186 and an opposing second end 188. Inside edge 184 and cutting surface 174 have a substantially continuous concave curvature extending between ends 186 and 188. Cutting surface 174 also extends laterally from inside edge 184 to an outer apex 190 of curved outside edge 185. This lateral extension of cutting surface 174 can be substantially flat or have a substantially concave curvature. Furthermore, cutting surface 174 extends laterally relative to interior surfaces 161 and 163 so as to form an inside angle θ which is less than 90°. In an alternative embodiment, angle θ could also be equal to or greater than 90°.

Figure 10:
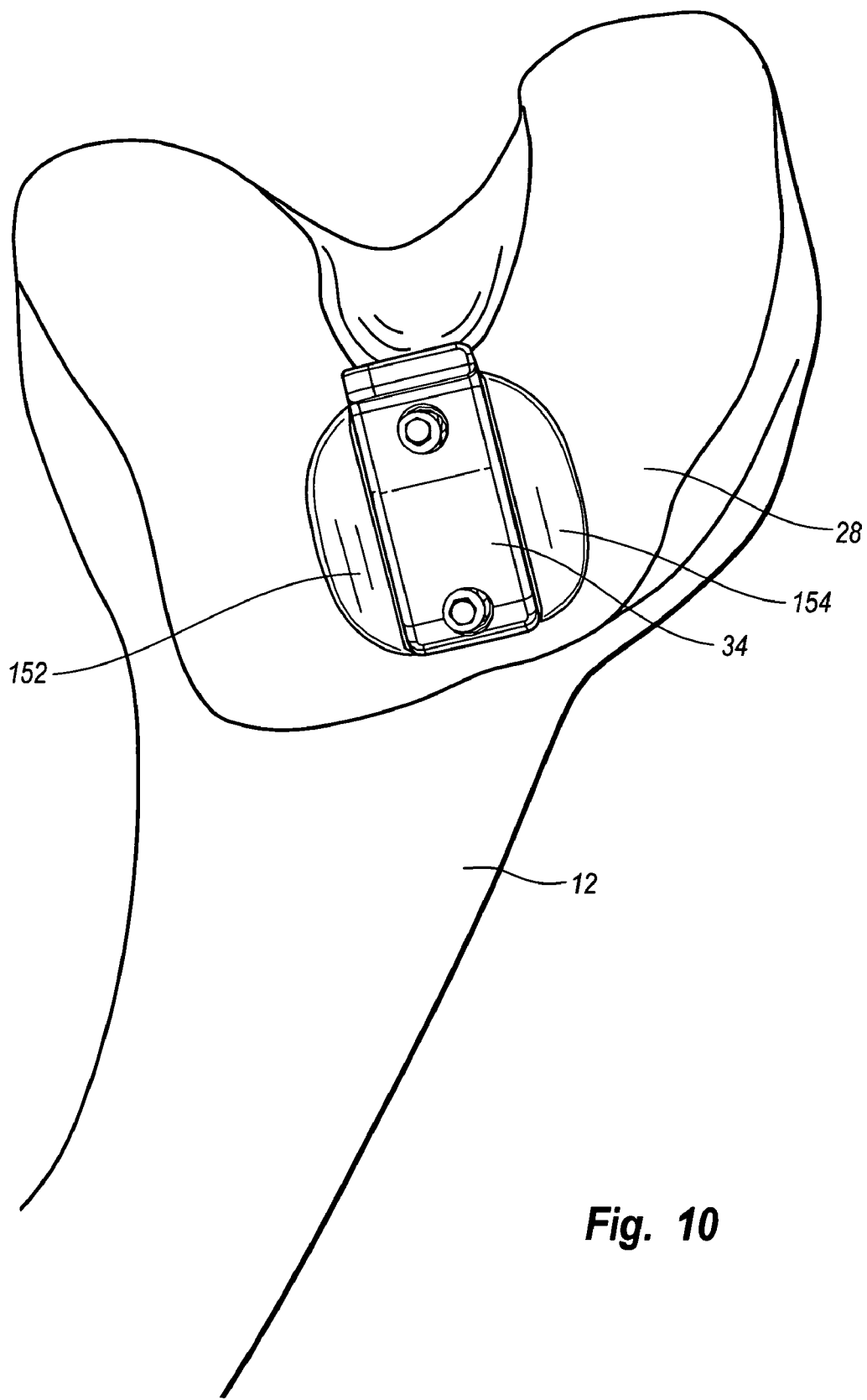
FIG. 10 is a perspective view of the femur shown in FIG. 6 having pockets formed thereon by the rasp shown in FIG. 7.

During use, handle 159 is coupled to a reciprocating driver which rapidly reciprocates rasp 156 along first cutting guide 34. As a result of the configuration of cutting heads 170 and 172, pockets 152 and 154, as depicted in FIG. 10, are formed on each side of first cutting guide 34. When viewed from a top plan view, each pocket has a generally semicircular configuration. When viewed from a transverse cross sectional view, each pocket 152 and 154 extends down into femur 12 in a substantially V-shape notch.

Figure 11:
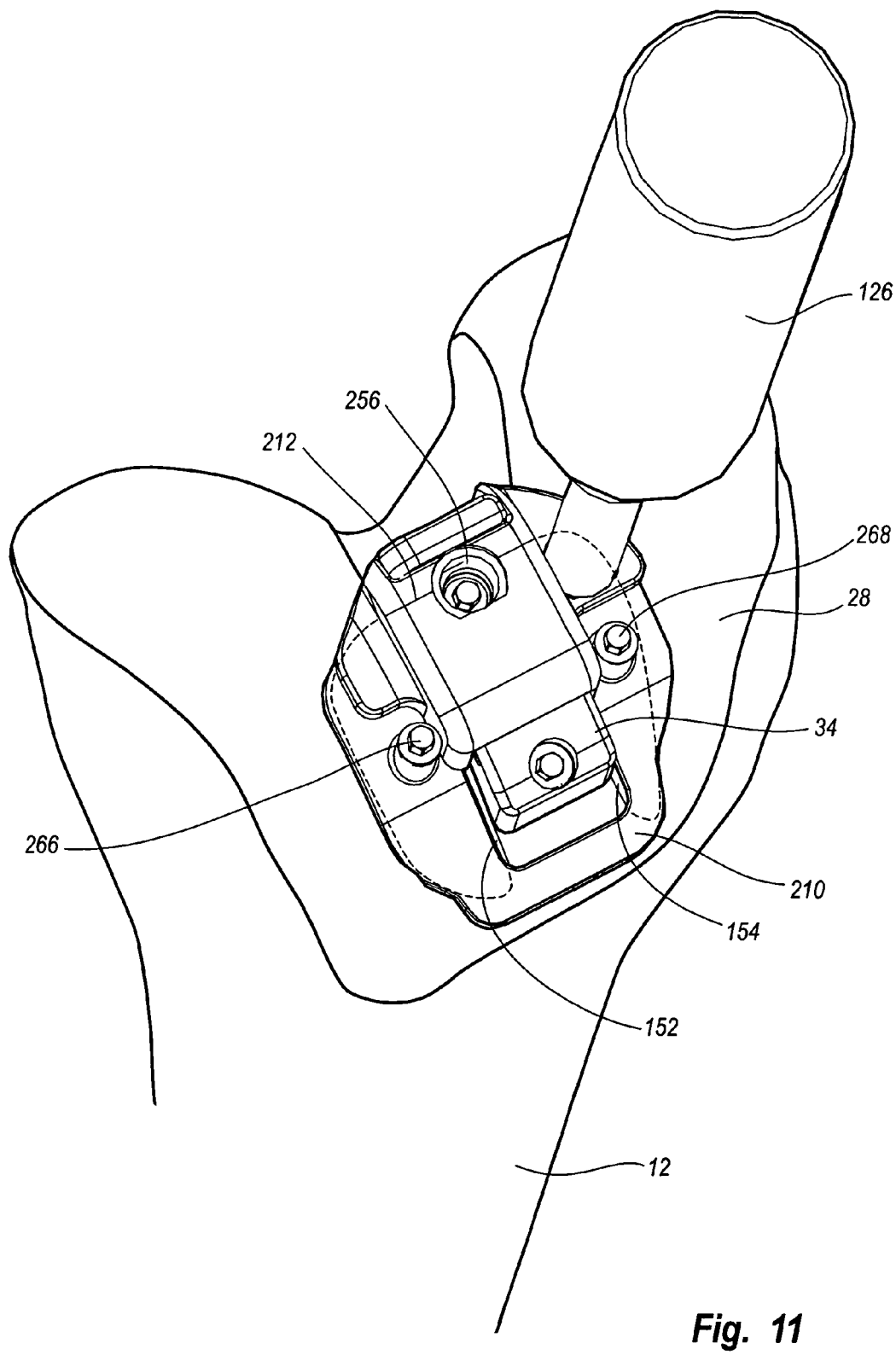
FIG. 11 is a perspective view of the femur shown in FIG. 10 having a second cutting guide and an alignment guide mounted on the first cutting guide.

Once pockets 152 and 154 are formed by removing the first portion of articulation surface 28, a second cutting guide is used to remove a second portion of articulation surface 28 that is covered by first cutting guide 34. By way of example, depicted in FIG. 11 is a second cutting guide 210 mounted on articulation surface 28 through the use of an alignment guide 212.

Figure 12:
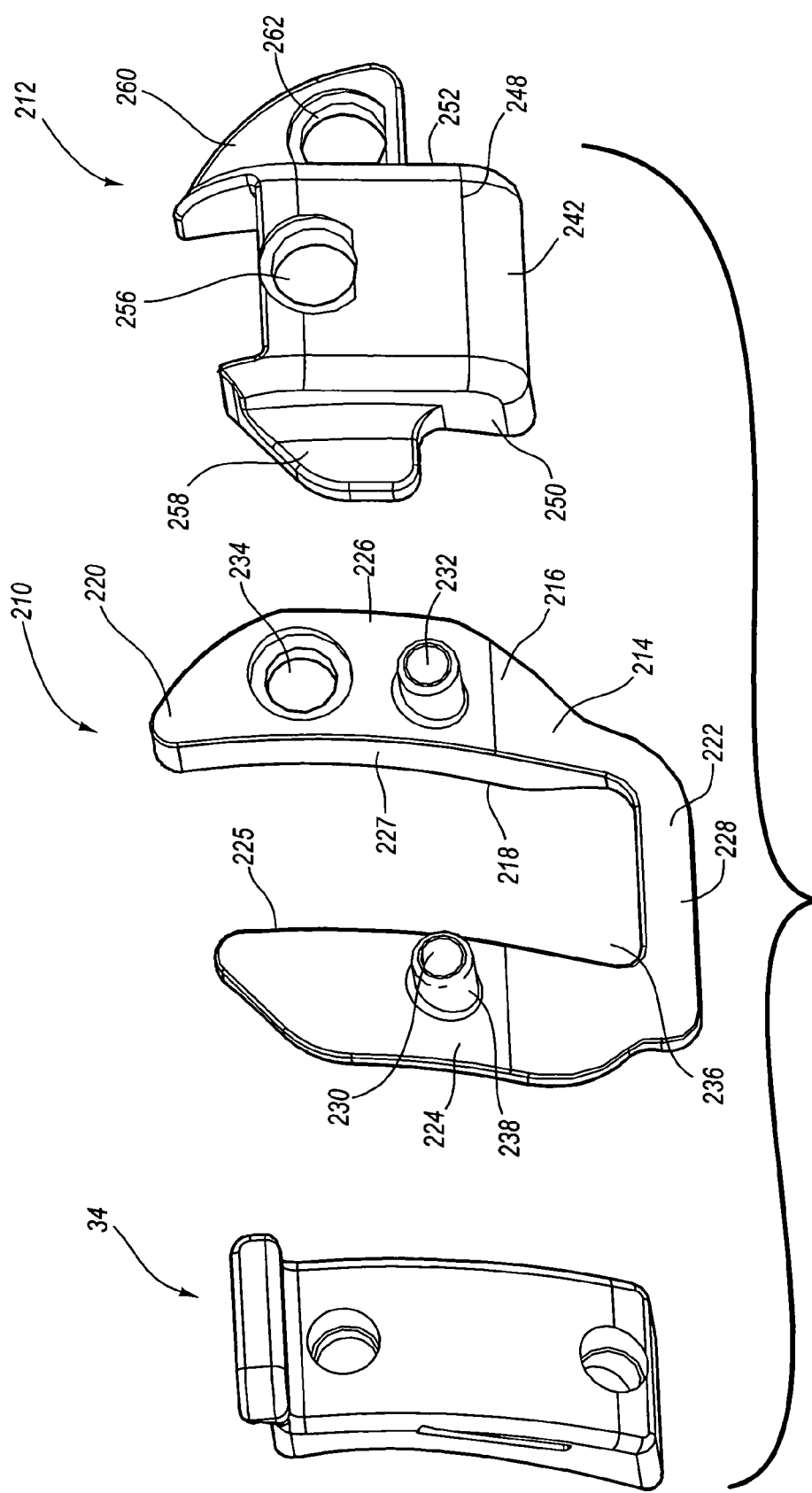
FIG. 12 is an exploded top perspective view of the first cutting guide, second cutting guide, and alignment guide shown in FIG. 11.
Figure 13:
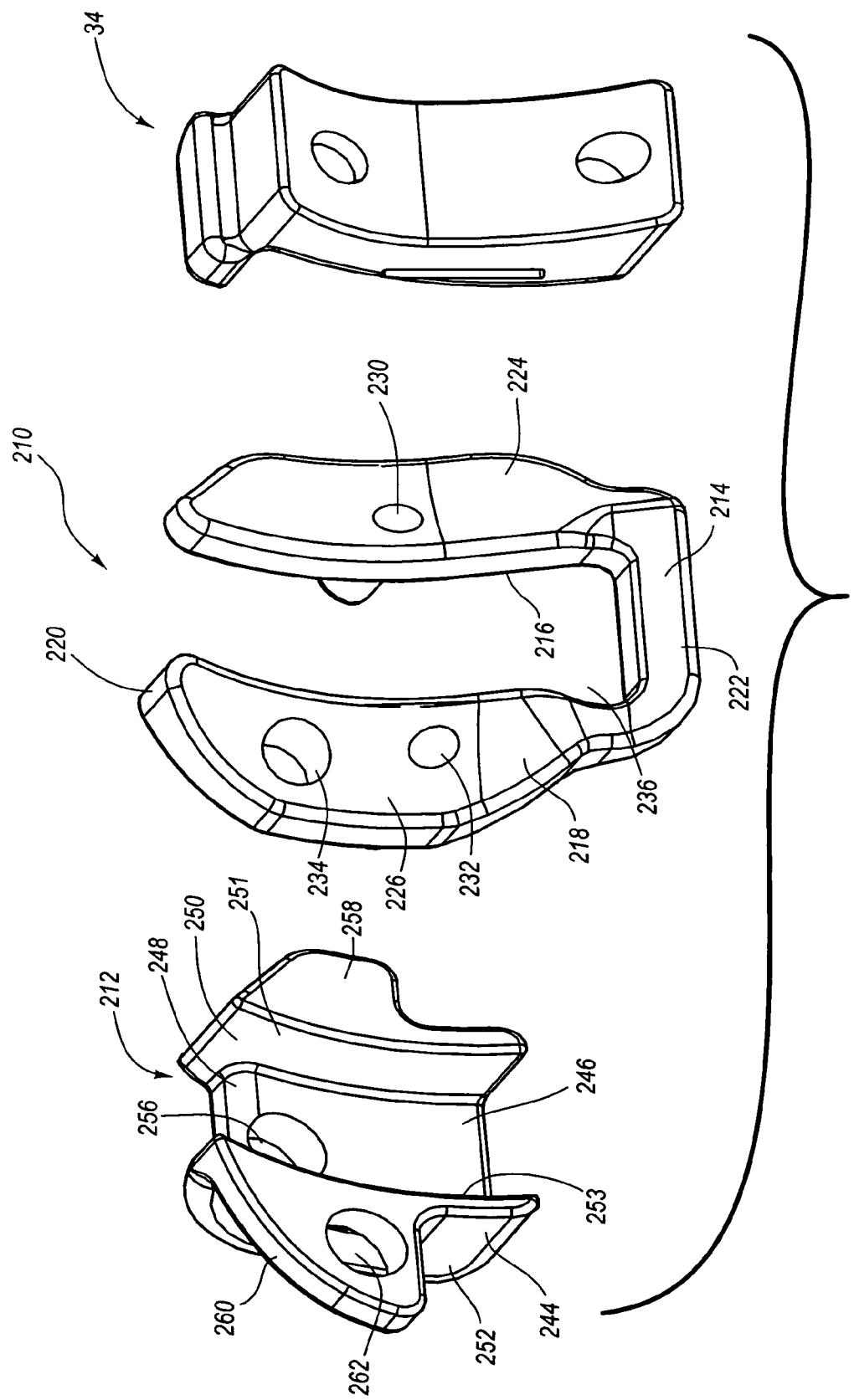
FIG. 13 is a bottom perspective view of the first cutting guide, second cutting guide, and alignment guide shown in FIG. 12.

As depicted in FIGS. 12 and 13, second cutting guide 210 has a substantially U-shaped body 214 having a top surface 216 and an opposing bottom surface 218. Each surface 216 and 218 extends between a first end 220 and an opposing second end 222. More specifically, body 214 comprises an elongated first arm 224, an elongated second arm 226, and a support 228 extending therebetween at second end 222. Each arm 224 and 226 has a corresponding inside face 225 and 227, respectively. Inside faces 225 and 227 are substantially linear and are disposed in substantially parallel alignment. As will be discussed below in greater detail, these surfaces act as guides for a rasp. During placement, each arm 224 and 226 is sized to fit within corresponding pockets 152 and 154. Support 228, however, is disposed outside of pockets 152 and 154. Extending between top surface 216 and bottom surface 218 on each arm 224 and 226 is a mounting hole 230 and 232, respectively. A tubular stem 238 encircles each mounting hole 230 and 238 and upwardly projects from top surface 216. A threading coupling hole 234 also extends through second arm 226.

Bounded between arms 224 and 226 is a channel 236. In the depicted embodiment, channel 236 has a substantially rectangular configuration and is slightly wider and longer than first cutting guide 34. As a result, as depicted in FIG. 11, second cutting guide 210 can be disposed on articulation surface 28 so that first cutting guide 34 is received within channel 236. An inside section of each pocket 152 and 154 is also disposed within channel 236 so that a smooth transition can be formed as a second rasp is used to resect the bone covered by first cutting guide 34.

As also depicted in FIGS. 12 and 13, alignment guide 212 comprises a body 244 having a channel 246 extending along the length thereof. Channel 246 is configured to receive first cutting guide 34 in a close tolerance fit. More specifically, body 244 comprises a top wall 248 having a pair of side walls 250 and 252 orthogonally, downwardly projecting from the sides thereof. Each side wall 250 and 252 has an interior surface 251 and 253, respectively. Interior surfaces 251 and 253 bound channel 246. An alignment hole 256 extends through top wall 248 so as to communicate with channel 246. Outwardly projecting from side walls 250 and 252 are wings 258 and 260, respectively. A coupling hole 262 extends through wing 260.

During use, alignment guide 212 is disposed on top surface 216 of second cutting guide 210 so that coupling holes 262 and 234 are in alignment. Tip 128 of handle 126 (FIG. 3) is then passed through coupling hole 262 and threaded into coupling hole 234 so as to temporarily rigidly secure alignment guide 212 and second cutting guide 210. It is also noted that tubular sleeves 238 on second cutting guide 210 can be used to help facilitate alignment and retention of alignment guide 212 on second cutting guide 210.

With alignment guide 212 secured to second cutting guide 210, handle 126 is used to selectively place alignment guide 212 over first cutting guide 34 so that arms 224 and 226 are received within corresponding pockets 152 and 154 as depicted in FIG. 11. As a result of the close tolerance between alignment guide 212 and first cutting guide 34, second cutting guide 210 is precisely set at the desired location for mounting.

In one embodiment of the present invention, means are provided for securing second cutting guide 210 to femur 12 independent of first cutting guide 34 and alignment guide 212. By way of example and not by limitation, mounting holes 230 and 232 are formed as previously discussed. Screws 266 and 268 are passed through mounting holes 230 and 232 so as to rigidly secure second guide 210 to femur 12. Screws 266 and 268 can have substantially the same configuration as previously discussed screws 90 and 92. However, because second cutting guide 210 is disposed directly on femur 12 within pockets 152 and 154, guide sleeves are not required within mounting holes 230 and 232. However, guide sleeves can still be used.

Figure 14:
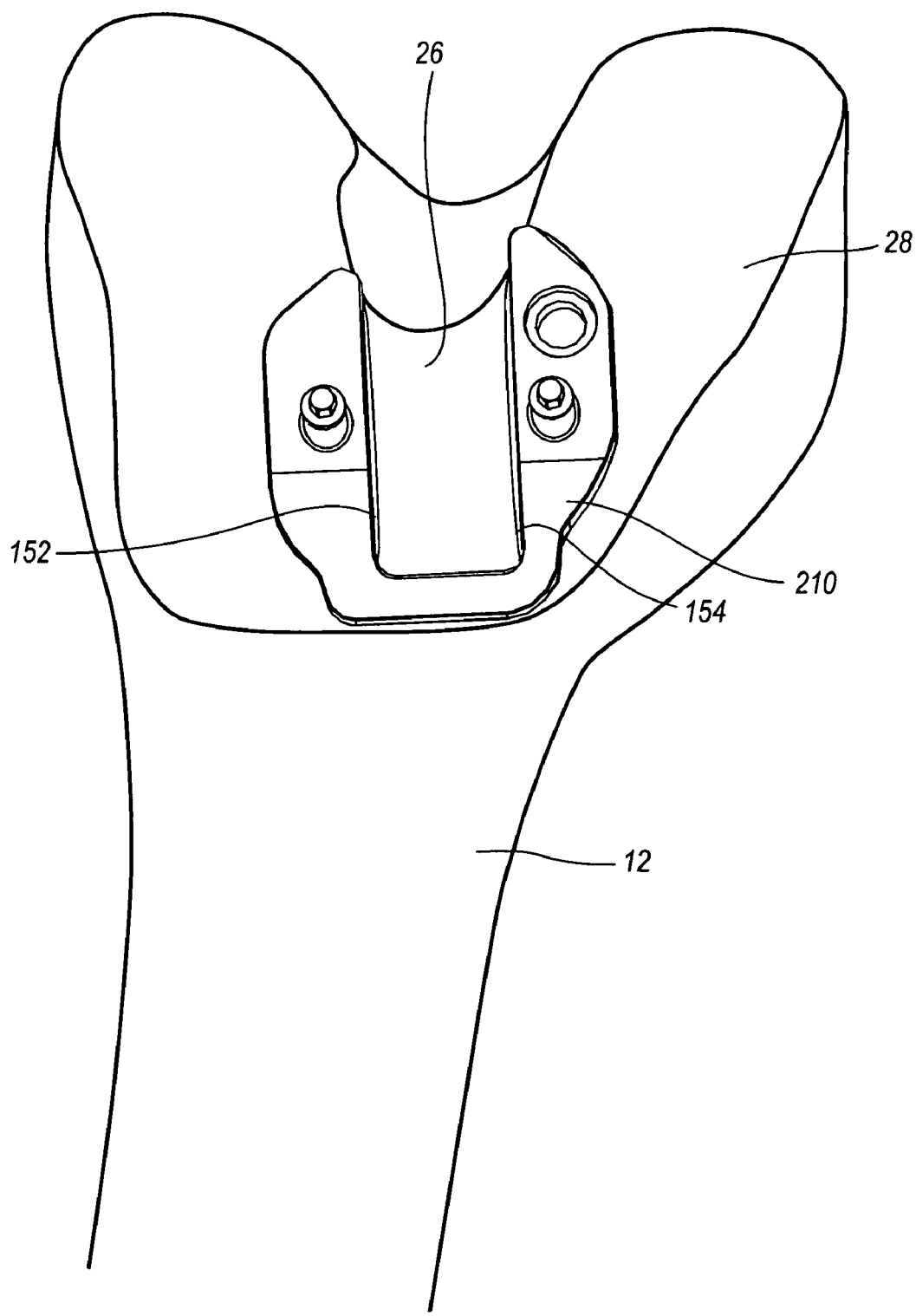
FIG. 14 is a perspective view of the femur shown in FIG. 11 wherein the first cutting guide and alignment guide have been removed.

It is noted that alignment hole 256 is aligned with mounting hole 86 of first cutting guide 34. During the mounting of screws 266 and 268, handle 126 or a second handle 126 can be passed through alignment hole 256 and coupled with screw 90 so as to further secure the fixed engagement between alignment guide 212, first cutting guide 34, and second cutting guide 210. Once second cutting guide 210 is secured in place, alignment guide 212 and first cutting guide 34 are removed as depicted in FIG. 14.

Figure 15:
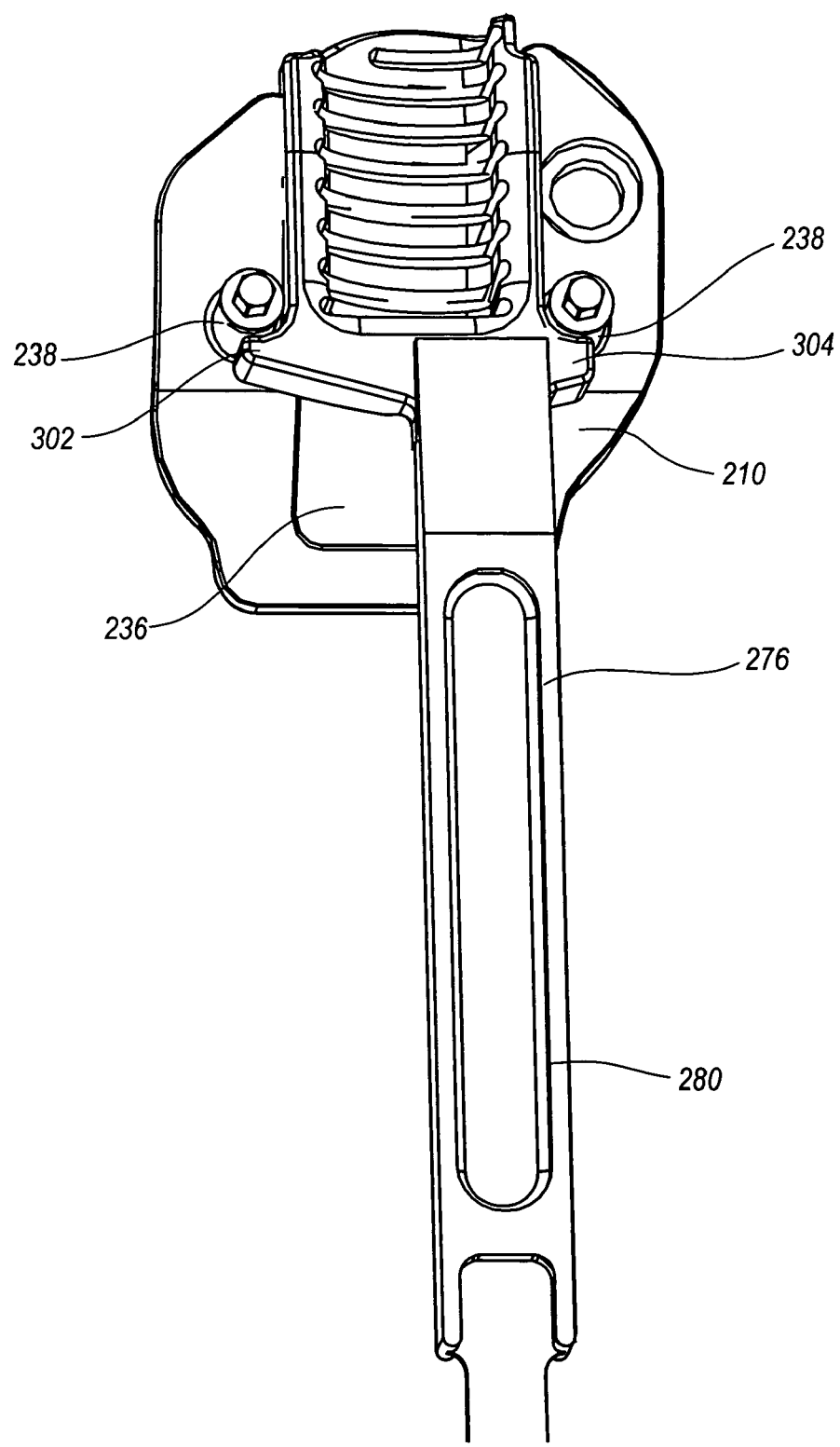
FIG. 15 is a perspective view of the second cutting guide shown in FIG. 14 having a rasp mounted thereon.
Figure 16:
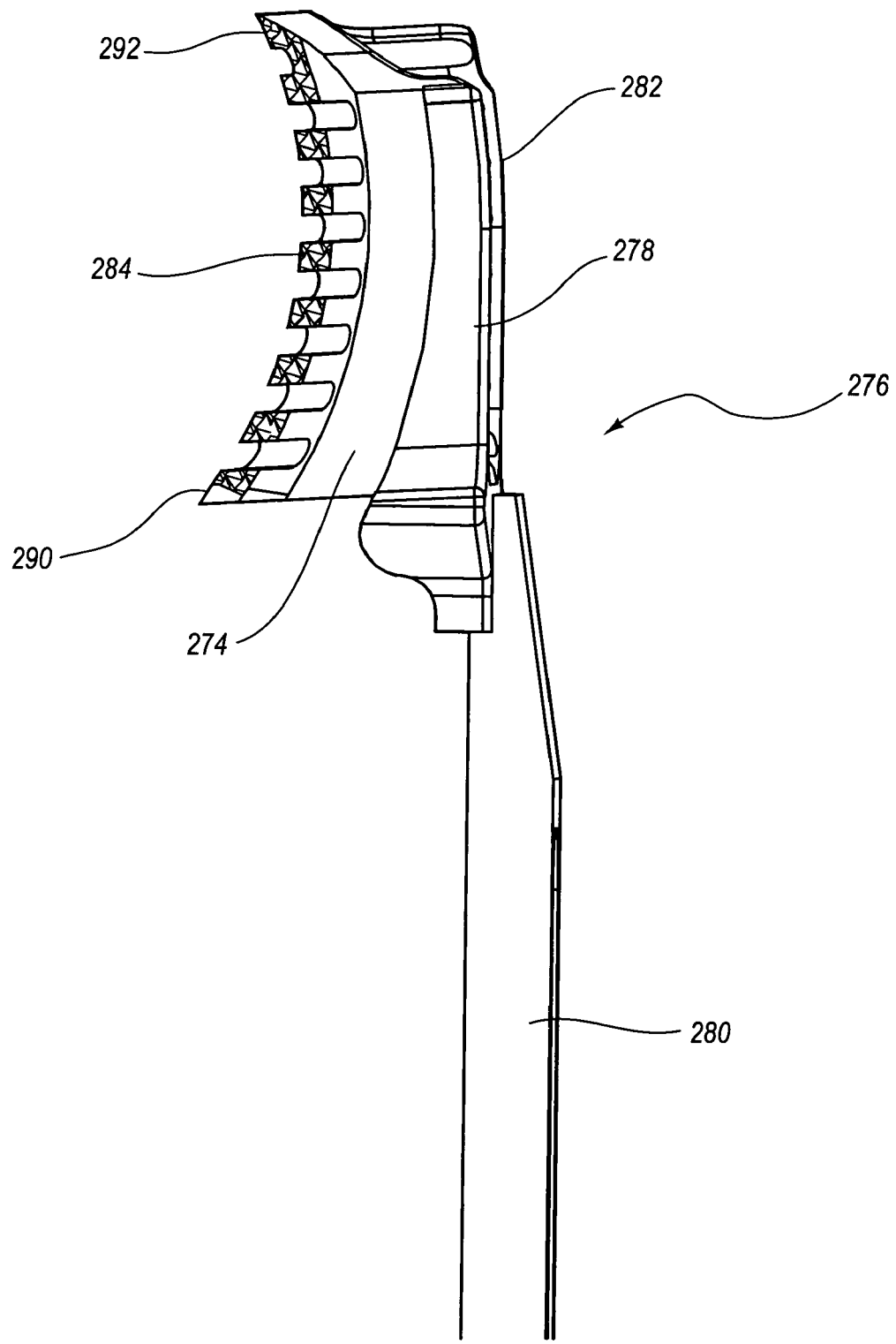
FIG. 16 is a side view of the rasp shown in FIG. 15.
Figure 17:
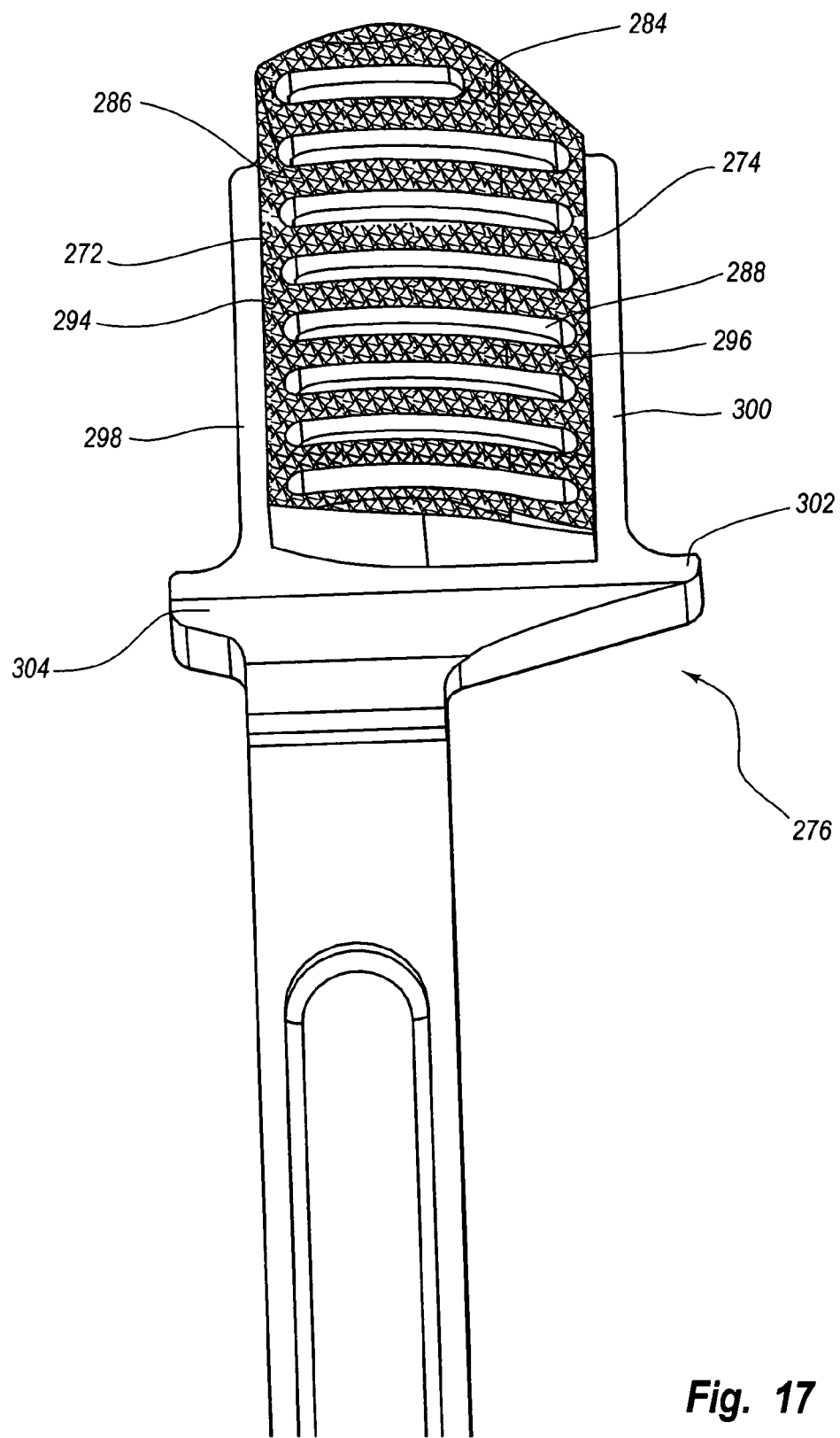
FIG. 17 is a bottom perspective view of the rasp shown in FIG. 15.

Depicted in FIG. 15, a rasp 276 is now used to remove the second portion of the articulation surface 28 which was previously covered by first cutting guide 34. As depicted in FIGS. 15-17, rasp 276 comprises a cutting head 278 having an elongated handle 280 attached thereto. Cutting head 278 has a top surface 282 and an opposing cutting surface 284 with side walls 272 and 274 extending therebetween. Sidewalls 272 and 274 are substantially linear and are disposed in substantially parallel alignment.

Cutting surface 284 is comprised of a plurality of cutting teeth 286. A plurality of spaced apart slots 288 extend between top surface 282 and cutting surface 284 so as to enable the remove of bone particles that are shaved off by cutting teeth 286. As depicted in FIG. 16, cutting surface 284 has a longitudinal dimension extending between a first end 290 and an opposing second end 292. Cutting surface 284 has a continuous concave curvature extending along this longitudinal surface. Likewise, as depicted in FIG. 17, cutting surface 284 has a transverse dimension extending between a first side 294 and a second side 296. Cutting surface 284 has a continuous concave curvature extending in this transverse dimension.

Outwardly projecting from side walls 272 and 274 are slide rails 298 and 300, respectively. A pair of stops 302 and 304 also outwardly project from the second end of cutting head 278. During use, cutting surface 284 is received within channel 236 of second cutting guide 210 so that side walls 272 and 274 of rasp 276 are disposed adjacent to inside faces 225 and 227 of second cutting guide 210. A reciprocating driver is connected with handle 280 so as to selectively reciprocate rasp 276. The second portion of articulation surface 28 is removed by cutting teeth 286 until slide rails 298 and 300 come to rest on top surface 216 of second cutting guide 210. During the reciprocating, it is noted that stops 302 and 304 interact with tubular sleeves 238 so as to prevent rasp 276 from extending to far forward on second cutting guide 210.

Once the second portion of articulation surface 28 is removed, second cutting guide 218 is removed from femur 12 so as to expose a final recessed pocket 310 in which the implant is to be mounted. Pocket 310 is bounded by a floor 312 having an encircling side wall 314 upstanding around the perimeter thereof. Pocket 310 has opposing sides 316 and 318 that extend between a proximal end 320 and an opposing distal end 322.

Due to the configuration of rasp 276, a rounded, elongated channel 324 is recessed along floor 312 in substantial alignment with where trochlear groove 28 was previously disposed. That is, channel 324 extends between opposing ends 320 and 322. Floor 312 also has a convex curvature that extends between opposing ends 320 and 322. As will be discussed below in greater detail, the configuration of recessed pocket 310 enables the formation of a low profile trochlear implant having substantially uniform thickness. Furthermore, the formation of pocket 310 produces a stable platform for the implant having a complementary configuration.

Once recessed pocket 310 is finished, a tunnel 330 is formed extending from pocket 310 to a location spaced apart from the articulation surface 28, such as medial side 14 or lateral side 16 of femur 12. Tunnel 330 can be formed by simply using a drill to manually form the tunnel. That is, tunnel 330 can be drilled by starting at recessed pocket 310 and extending to the lateral or medial side of the femur 12. Other techniques, guides and instruments for forming tunnel 330 are disclosed in U.S. patent application Ser. No. 10/901, 941, filed Jul. 28, 2004 which is incorporated herein by specific reference.

Figure 19:
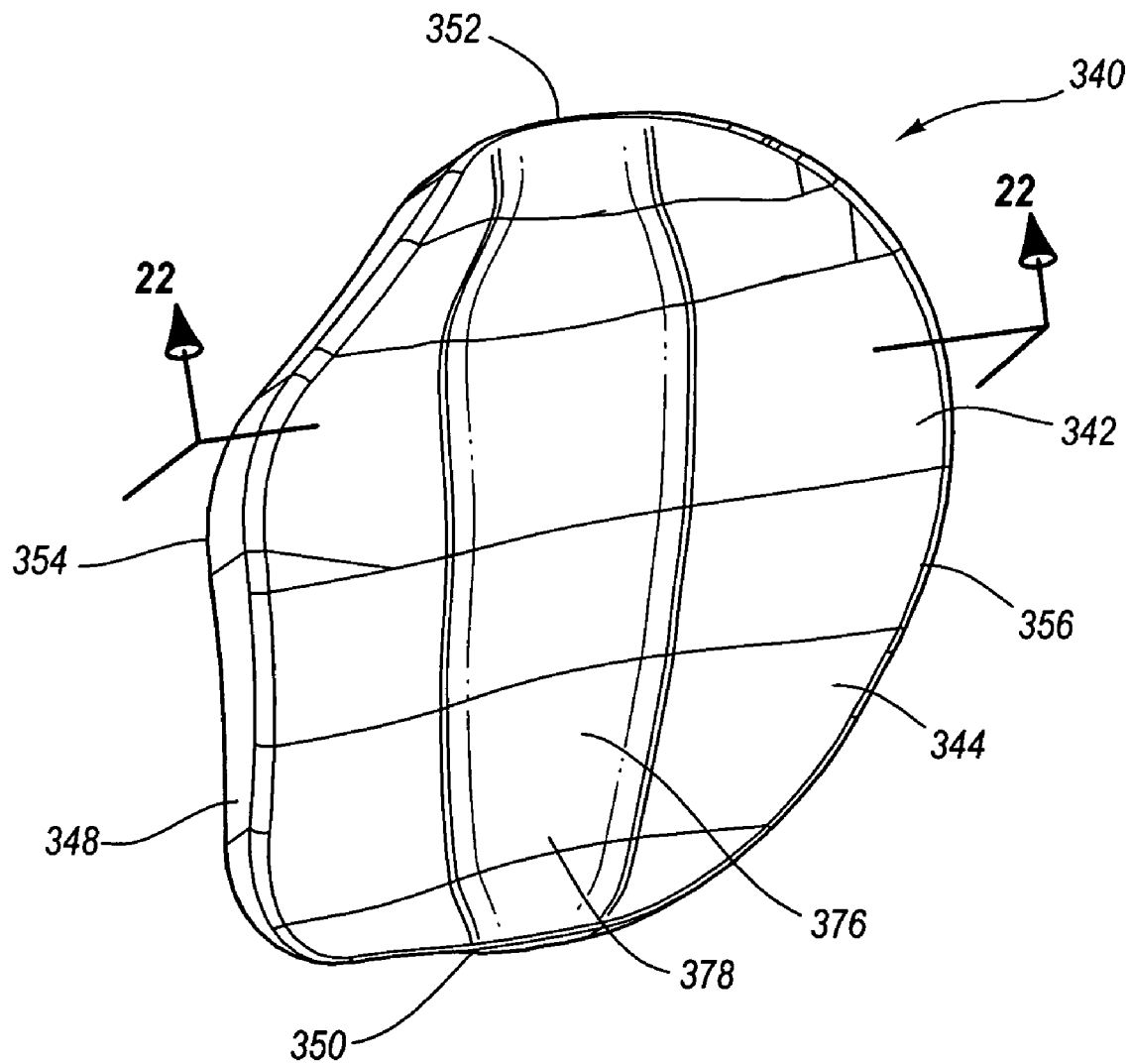
FIG. 19 is a top perspective view of a trochlear implant.
Figure 20:
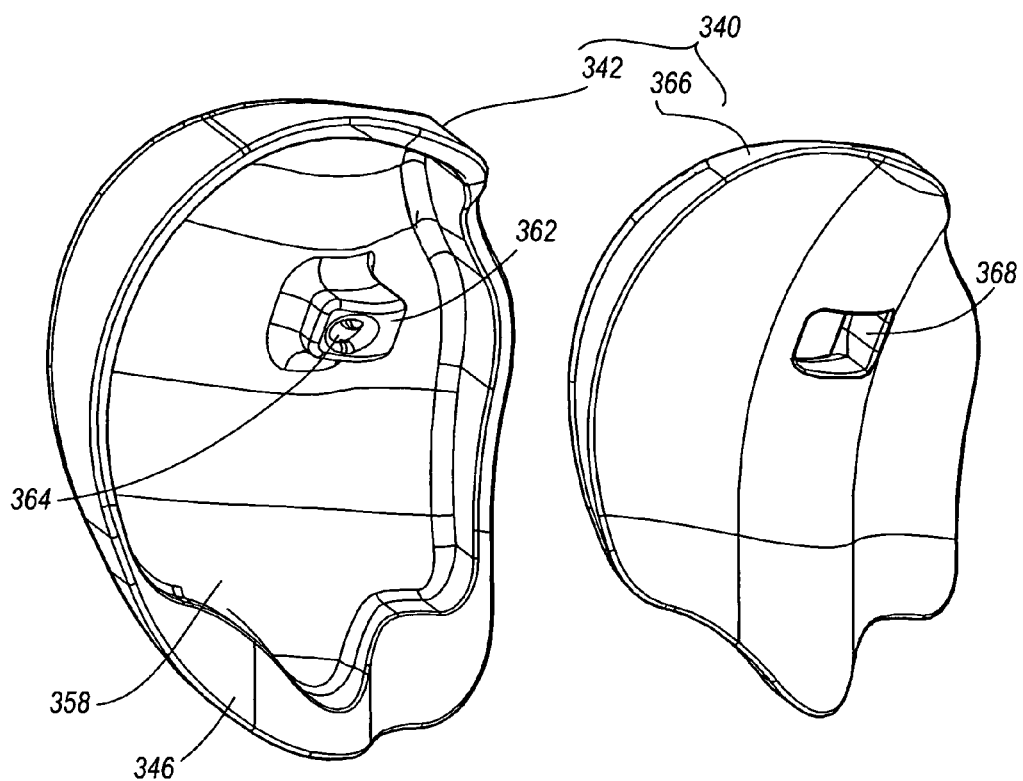
FIG. 20 is a bottom perspective exploded view of the implant shown in FIG. 19.

Once tunnel 330 is formed, a trochlear implant is then secured within the recessed pocket 310. Depicted in FIGS. 19 and 20 is one embodiment of a trochlear implant 340 incorporating features of the present invention. Trochlear implant 340 comprises a body 342 having an articular surface 344 and an opposing bottom surface, 346 that each extend to a perimeter edge 348. Body 342 is further defined as having a proximal end 350 and a distal end 352 each extending between a lateral side 354 and a medial side 356. Articular surface 344 is formed having an elongated channel 376 extending between proximal end 350 and distal end 352 substantially centrally between sides 354 and 356. Channel 376 forms at least a portion of the resurfaced trochlear groove in which the patella rides.

Figure 22:
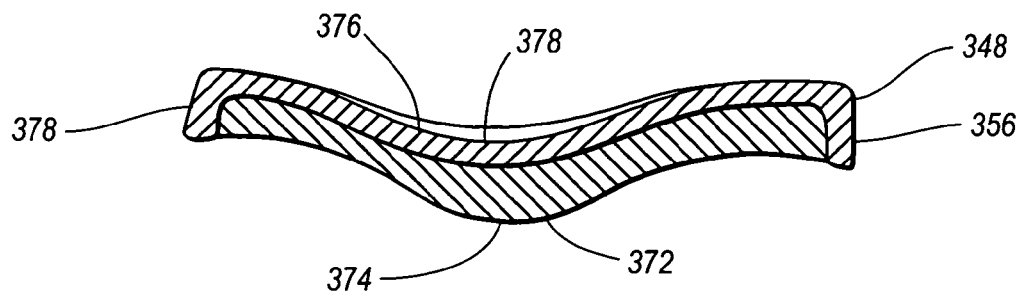
FIG. 22 is a cross sectional side view of the implant shown in FIG. 19 along line 22-22.

In one embodiment viewed in a plane extending between sides 354 and 356 (FIG. 22), channel 376 has a bottom 378 with a concave curvature. The surfaces extending from the concave curvature at bottom 378 to perimeter edge 348 at each side 354 and 356 are typically not concave. Rather, these surfaces are typically substantially flat so as to form a substantially V-shaped transverse cross section with rounded bottom or have a substantially convex curvature. It is also appreciated that articular surface 344 has a smooth continuous convex curvature that extends between opposing ends 350 and 352 (FIG. 19).

Figure 21:
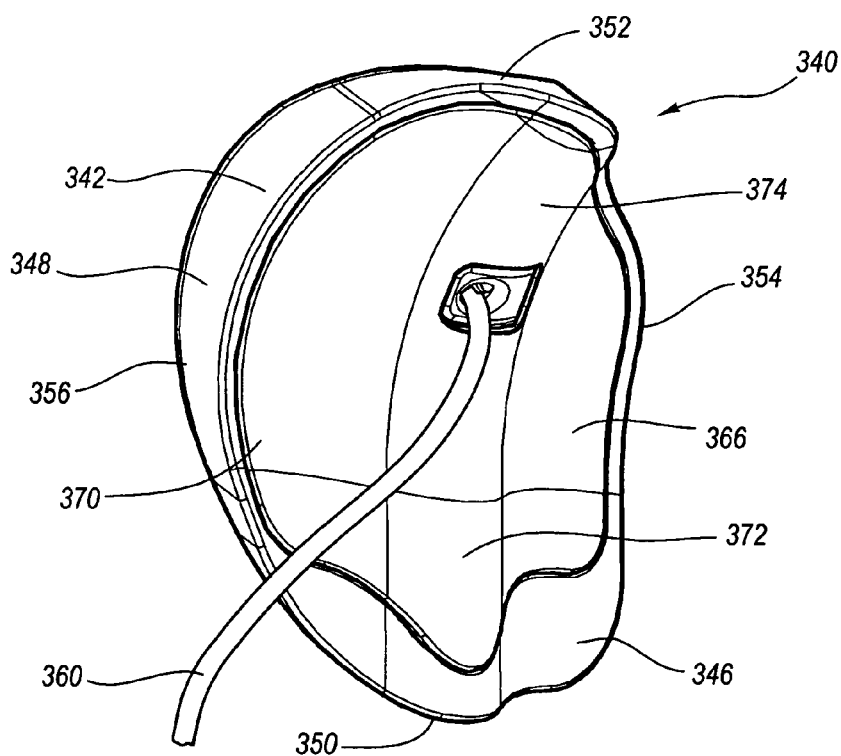
FIG. 21 is a bottom perspective view of the implant shown in FIG. 19 having a line coupled therewith.

Depicted in FIG. 21, a flexible line 360 is secured to trochlear implant 340. As used in the specification and append claims, the term "line" is broadly intended to include wire, cable, cord, suture, braded line, combinations thereof or any other type of flexible filament. The line can be made of metal, alloys, synthetics, composites, or any other desired material. In one embodiment of the present invention the line comprises braded filaments of a cobalt chrome alloy having a diameter in a range between about 0.25 mm to about 5 mm with about 0.5 mm to about 3 mm being more common and about 0.5 mm to about 2 mm being most common. Other dimensions can also be used. The line can be of any desired length.

In one embodiment, the line can also be defined in that for an unsupported length of line of 4 cm, the line has substantially no compressive strength. In yet other embodiments, for an unsupported length of line of 4 cm, the line fails under buckling when an axial compressive load of 0.25 Newtons (N), 1 N, 2 N, 5 N, 20 N, or 50 N is applied. That is, different lines can be used that fail under different loads. Stiffer lines can also be used.

It is also appreciated that the line can be static or resiliently stretchable. In one embodiment where the line is resiliently stretchable, the line can be comprised of a material having shape memory of pseudo elastic properties. One example of such a material is a nickel titanium alloy sold under the name Nitinol. In yet other embodiment, it is appreciated that sections of the line could be replaced with a spring member such as a coiled spring or rubber or bungee type member.

Turning to FIG. 20, formed on bottom surface 346 of body 342 is a pocket 358. In the embodiment depicted, a post 362 projects from within pocket 358. A constricting passage 364 extends through post 362 and is configured to hold flexible line 360. Specifically, line 360 is formed with an enlarged head at one end so that when line 360 is passed through passage 364, the enlarged head is captured within passage 364. Secured within pocket 358 is an inlay 366 of a porous bone ingrowth material. Inlay 366 has an opening 368 formed thereon through which post 362 extends.

Returning to FIG. 21, bottom surface 346 and inlay 366 combine to form a bone apposition surface 370 of trochlear implant 340. Bone apposition surface 370 has a configuration complementary to the formation of recessed pocket 310 formed on femur 12. Bone apposition surface 370 also typically has a configuration complementary to articular surface 344. Specifically, bone apposition surface 370 is formed having a rounded, outwardly projecting ridge 372 that extends between proximal end 350 and distal end 352, substantially centrally between sides 354 and 356. When viewed in a plane extending between sides 354 and 356 (FIG. 22), ridge 372 terminates at an apex 374 having a convex curvature. The side surfaces of ridge 372 extending to sides 354 and 356 are typically substantially flat or have a concave curvature.

Ridge 372 is typically aligned with channel 376 so that trochlear implant 340 can have a substantially uniform thickness. For example, in one embodiment bone apposition surface 370 can be substantially complementary to articular surface 344 so that implant 340 has a substantially uniform thickness between surfaces 344 and 370. In other embodiments, implant 340 may be slightly tapered along perimeter edge 348. Thus, at all locations at least 2 mm in from the perimeter edge 348, body 342 has a thickness extending between the bone apposition surface 370 and the articular surface 344 that does not vary by more than 30%, 20%, or more commonly 15%. Other percentages can also be used. The actual thickness depends on the desired implant and is typically in a range between about 3 mm to about 10 mm.

Ridge 372 is also configured to be complementarily received within channel 324 formed on recessed pocket 310. Bone apposition surface 370 thus also has a continuous concave curvature extending between opposing ends 350 and 352. Because of the unique method in which pocket 310 can be formed, bone apposition surface 370 can be formed having a smooth surface with no stepped shoulders or corners as required in many conventional implants.

Because implant 340 is configured to fit within pocket 310, implant 340 has an outer perimeter having an asymmetrical configuration complementary to pocket 310. In one embodiment, articular surface 344 of implant 340 has a centroidial location. Articular surface 344 has a maximum radius extending from the centroidial location to perimeter edge and a minimum radius extending from the centroidial location to the perimeter edge, the minimum radius not being less than 70% and more commonly not being less than 80% of the maximum radius. Other dimensions can also be used.

It is appreciated that implant 340 as discussed above and depicted herein is only one example of an implant that can be used in association with the present invention. In alternative embodiments, implant 340 can have a variety of different sizes, shapes, configurations, components, and other modifications. For example, spikes or other forms of projections can be formed projecting from bone apposition surface 370. Furthermore, conventional implants using conventional mounting techniques can be secured within pocked 310. Examples of alternative implants that can be used with the present invention are disclosed in the U.S. patent application Ser. No. 10/901,941 which was previously incorporated by reference.

Figure 18:
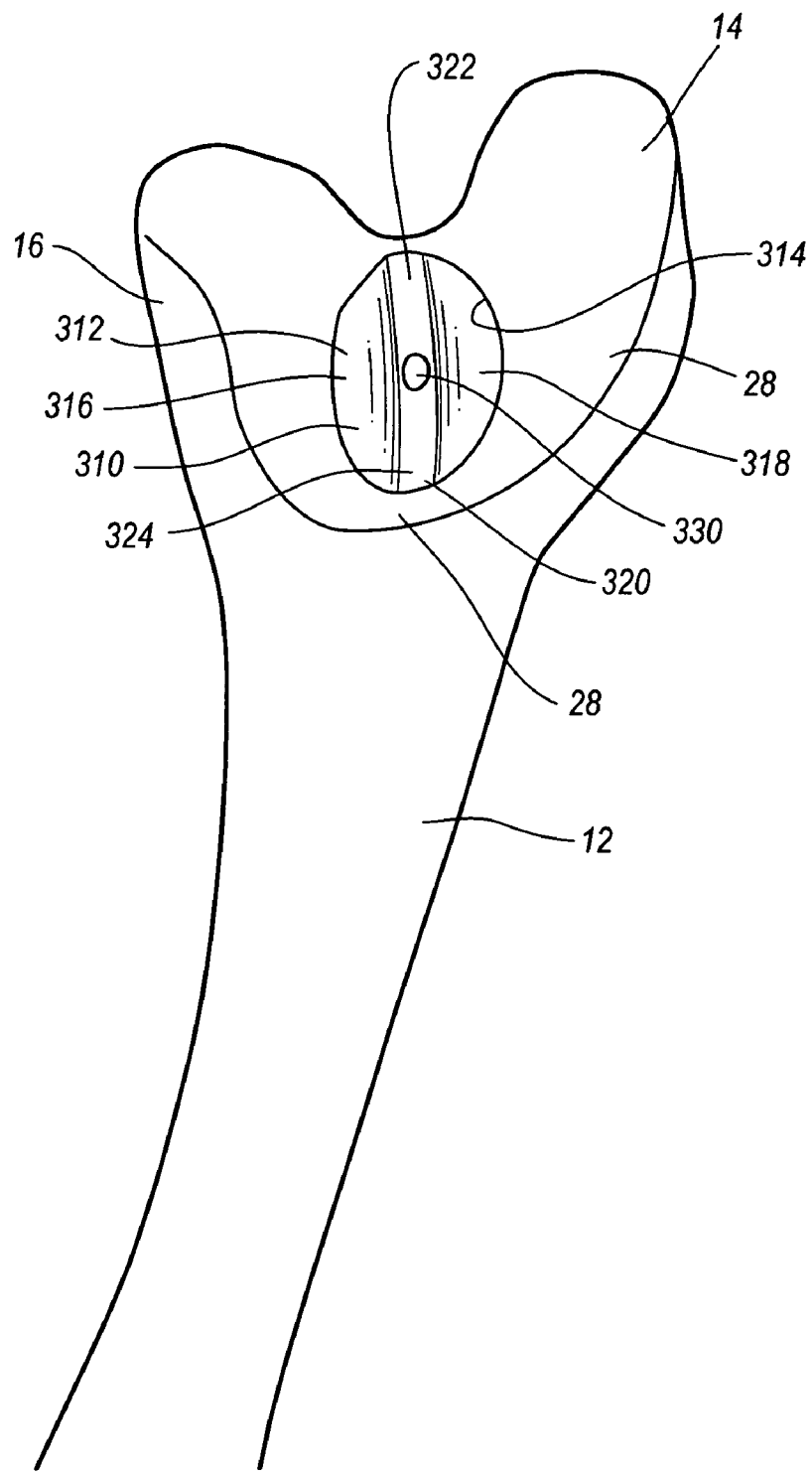
FIG. 18 is a perspective view of the femur shown in FIG. 14 having a completed pocket formed thereon by the rasp shown in FIG. 15.
Figure 23:
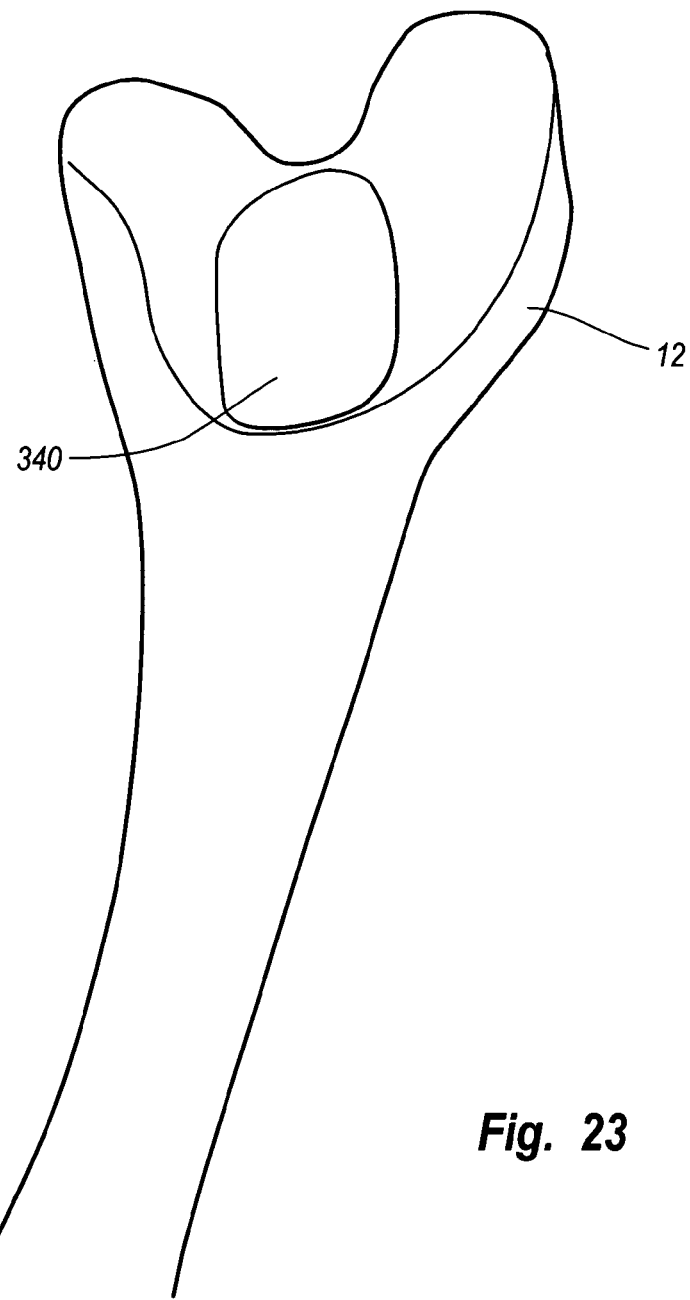
FIG. 23 is a perspective view of the femur shown in FIG. 18 having the implant of FIG. 19 mounted in the pocket thereof.

Finally, turning to FIG. 23, trochlear implant 340 is secured within recessed pocket 310 of femur 12. In the depicted embodiment, this is accomplished by passing line 360 (FIG. 21) within tunnel 330 (FIG. 18) and then using a tensioner and anchor assembly to secure line 360 within tunnel 330. Examples of bone anchors and tensioners that can be used in association with the present invention are disclosed in U.S. patent application Ser. No. 10/901,941 which was previously incorporated by reference. Again, other conventional techniques can be used to secure implant within pocket 360. In such other techniques, line 360 can be eliminated.

The above disclosure discusses a number of different guides, rasps and other related instruments, implants and methods. It is appreciated that the individual components and sub-combination of components are novel and can be used independently or mixed and matched with other conventional systems. For example, where the cutting guides help define the area that is to be resected, other cutting instruments, such as mills, burs, and other rasp configurations can be used to resect the bone. Likewise, in contrast to using a two step process to form pocket 310, it is appreciated that three or more consecutive and releasably connecting guides can be used to form pocket 310 using three or more resecting steps. Likewise, the rasps disclosed herein can be broken down into smaller rasps which can be used sequentially to form pocket 310.

Furthermore, the depicted embodiment of the present invention operates by first removing an outer portion of pocket 310 and then an inner portion of the pocket 310. In other embodiments, it is appreciated that the guide system can be modified so as to operate in reverse. Alternatively, the guide system can be designed so as to remove one side of the pocket and then the adjacent side. Other modifications are also envisioned by the present invention.

Different features of the present invention provide a number of benefits over conventional systems and methods. For example, in contrast to many conventional processes which require the removal of an entire articulation surface for the mounting of an implant, the present invention enables the resurfacing of an isolated location on the articulation surface. As a result, the procedure is less invasive and recovery time is increased. The guide systems of the present invention enable the formation of the pocket while minimizing retraction of soft tissue, minimizing the amount of bone removal, and minimize the time required to remove the bone and mount the implant. The guide system is also unique in that the guide system is largely mounted only over the area of the articulation surface that is to be resurfaced. As a result, the potential for unintentional damage to the portion of the surrounding articular surface that is not to be resurfaced is minimized. Another advantage of the present invention is that it provides a system that is easy to mount and use on uneven or irregular surfaces, is easy to operate, and is easy to remove. The present invention also provides other advantages which will be apparent to those skilled in the art.

The present invention may be embodied in still other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A guide system for use in resecting at least a portion of a joint articulation surface on a bone, the system comprising:
   a first cutting instrument having a first cutting instrument guide surface;
   a mounting template comprising a base having at least two support legs projecting therefrom;
   a first cutting guide removably connected to the mounting template, the first cutting guide having a cutting guide surface complementary to the cutting instrument guide surface; and
   means for securing the first cutting guide to the bone independent of the mounting template, whereby the first cutting guide is adapted to guide the cutting instrument during the resection of the joint articulation surface on the bone.

2. The guide system as recited in claim 1, wherein the base of the mounting template has a bottom surface, the at least two support legs comprising at least three spaced apart support legs projecting from the bottom surface of the base.

3. The guide system as recited in claim 1, wherein the base of the mounting template has a top surface and an opposing bottom surface with an opening extending therebetween, the first cutting guide being removably disposed within the opening.

4. The guide system as recited in claim 1, further comprising a locking brace removably connected to the mounting template and removably connected to the first cutting guide.

5. The guide system as recited in claim 4, wherein a slot is formed on the first cutting guide, the locking brace being slidably received within the slot so as to removably connect the locking brace to the first cutting guide.

6. The guide system as recited in claim 4, further comprising a handle having a threaded tip, the threaded tip removably connecting the locking brace to the mounting template.

7. The guide system as recited in claim 1, wherein the first cutting guide has a bottom surface extending between a pair of opposing side walls, the opposing side walls being substantially linear and disposed in substantially parallel alignment.

8. The guide system as recited in claim 1, wherein the means for securing comprises at least one mounting hole formed on the first cutting guide and a fastener adapted to pass through the at least one mounting hole and engage the bone.

9. The guide system as recited in claim 1, wherein the cutting guide has a top surface and an opposing bottom surface each extending between a first end and an opposing second end, a stop upwardly projecting from the top surface at the first end.

10. The guide system as recited in claim 1, wherein the means for securing comprises a pair of spaced apart mounting holes formed on the cutting guide and a pair of fasteners, each fastener being adapted to pass through a corresponding mounting hole and engage the bone.

11. The guide system as recited in claim 1, wherein the first cutting instrument comprises a rasp comprising a body having a channel formed thereon, the channel being configured to receive the first cutting guide such that the rasp can slideably reciprocate along the first cutting guide, the rasp further comprising a rasping head projecting from the body on opposing sides of the channel to define a cutting surface on each rasping head, at least a portion of each cutting surface having a concave curvature, and each cutting surface having cutting teeth formed thereon.

12. The guide system as recited in claim 11, wherein the body comprises a pair of opposing side walls and a top wall extending therebetween, each side wall having an opposing inside face that is substantially linear and disposed in substantially parallel alignment with the other inside face.

13. The guide system as recited in claim 12, wherein each rasping head projects from a corresponding side wall of the body so that an inside angle less than 90° is formed between the inside face of each side wall of the body and the cutting surface of the corresponding rasping head.

14. The guide system as recited in claim 11, wherein each cutting surface has a perimeter edge with a generally semi-circular configuration.

15. The guide system as recited in claim 11, wherein each cutting surface has a substantially linear inside edge extending between a first end and an opposing second end, the inside edge having a concave curvature.

16. A guide system for use in resecting at least a portion of a joint articulation surface on a bone, the system comprising:
   a first cutting instrument having a first cutting instrument guide surface;
   a second cutting instrument having a second cutting instrument guide surface;
   a first cutting guide, the first cutting guide having a cutting guide surface complementary to the first cutting instrument guide surface;
   a second cutting guide, the second cutting guide having a second cutting guide surface complementary to the second cutting instrument guide surface;
   an alignment guide releasably engaging the first cutting guide and the second cutting guide so that the first cutting guide is held fixed relative to the second guide;
   means for securing the first cutting guide to the bone independent of the second cutting guide and the alignment guide, whereby the first cutting guide is adapted to guide the first cutting instrument during a first resection of the joint articulation surface on the bone; and
   means for securing the second cutting guide to the bone independent of the first cutting guide and the alignment guide, whereby the second cutting guide is adapted to guide the second cutting instrument during a second resection of the joint articulation surface on the bone.

17. The guide system as recited in claim 16, wherein the first cutting guide has a bottom surface extending between a pair of opposing side walls, the opposing side walls being disposed in substantially parallel alignment.

18. The guide system as recited in claim 16, wherein the second cutting guide has a top surface and an opposing bottom surface with an opening extending therebetween, the first cutting guide being received within the opening of the second cutting guide.

19. The guide system as recited in claim 18, wherein the second cutting guide has a substantially U-shaped configuration, the second cutting guide only partially bounding the opening.

20. The guide system as recited in claim 16, further comprising an elongated handle having a tip, the tip engaging the alignment guide and the second cutting guide.

21. The guide system as recited in claim 16, wherein the alignment guide has a channel formed therein, the first cutting guide being at least partially received within the channel of the alignment guide so that the alignment guide engages the first cutting guide.

22. The guide system as recited in claim 16, further comprising:
the first cutting guide having a top surface and an opposing bottom surface with a hole extending therebetween; and
the alignment guide having a top surface and an opposing bottom surface with a hole extending therebetween, the hole of the first cutting guide being aligned with the hole of the alignment guide.

23. The guide system as recited in claim 16, wherein the means for securing the first cutting guide comprises a pair of spaced apart holes formed on the first cutting guide and a pair of fasteners, each fastener being adapted to pass through a corresponding hole and engage the bone.

24. The guide system as recited in claim 16, wherein the means for securing the second cutting guide comprises a pair of spaced apart holes formed on the second cutting guide and a pair of fasteners, each fastener being adapted to pass through a corresponding hole and engage the bone.

25. A guide system for use in guiding a cutting instrument having a cutting instrument guide surface to resect at least a portion of a joint articulation surface on a bone, the system comprising:
a first cutting instrument having a first cutting instrument guide surface;
a mounting template comprising a base having at least two support legs projecting therefrom;
a first cutting guide removably connected to the mounting template, the first cutting guide having a cutting guide surface complementary to the cutting instrument guide surface; and
a first fastener adapted to secure the first cutting guide to the bone independent of the mounting template, whereby the first cutting guide is adapted to guide the cutting instrument during a first resection of the joint articulation surface on the bone.

26. The guide system as recited in claim 25, wherein the first cutting instrument comprises one of a rasp, a mill, and a burr.

27. The guide system as recited in claim 25, wherein the cutting instrument comprises a rasp comprising a body having a channel formed thereon, the channel being configured to receive the first cutting guide such that the rasp can slideably reciprocate along the first cutting guide, the rasp further comprising a rasping head projecting from the body on opposing sides of the channel to define a cutting surface on each rasping head, at least a portion of each cutting surface having a concave curvature, and each cutting surface having cutting teeth formed thereon.

28. The guide system as recited in claim 25, further comprising:
a second cutting instrument having a second cutting instrument guide surface; and
a second fastener adapted to secure the second cutting guide to the bone independent of the first cutting guide and the mounting template, whereby the second cutting guide is adapted to guide the second cutting instrument during a second resection of the joint articulation surface on the bone.

* * * * *